(12) United States Patent
Shaltiel-Karyo et al.

(10) Patent No.: US 8,546,330 B2
(45) Date of Patent: Oct. 1, 2013

(54) COMPOSITIONS AND METHODS FOR TREATMENT OF NEURODEGENERATIVE DISEASES

(75) Inventors: Ronit Shaltiel-Karyo, Ramat-HaSharon (IL); Ehud Gazit, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 110 days.

(21) Appl. No.: 13/255,244

(22) PCT Filed: Mar. 9, 2010

(86) PCT No.: PCT/IL2010/000193
§ 371 (c)(1),
(2), (4) Date: Sep. 8, 2011

(87) PCT Pub. No.: WO2010/103515
PCT Pub. Date: Sep. 16, 2010

(65) Prior Publication Data
US 2011/0319334 A1     Dec. 29, 2011

Related U.S. Application Data

(60) Provisional application No. 61/202,523, filed on Mar. 9, 2009.

(51) Int. Cl.
*A61K 38/01*     (2006.01)
(52) U.S. Cl.
USPC .............. 514/7.8; 436/86; 514/17.7; 530/327
(58) Field of Classification Search
None
See application file for complete search history.

(56) References Cited

U.S. PATENT DOCUMENTS

| 2006/0036073 A1 | 2/2006 | Windisch |
| 2008/0200397 A1 | 8/2008 | Windisch et al. |

FOREIGN PATENT DOCUMENTS

| WO | WO 01/60974 | 8/2001 |
| WO | WO 02/04482 | 1/2002 |
| WO | WO 2008/003943 | 1/2008 |
| WO | WO 2008/142579 | 11/2008 |
| WO | WO 2010/103515 | 9/2010 |

OTHER PUBLICATIONS

Communication Relating to the Results of the Partial International Search Dated Jun. 28, 2010 From the International Searching Authority Re. Application No. PCT/IL2010/000193.
International Search Report and the Written Opinion Dated Sep. 15, 2010 From the International Searching Authority Re. Application No. PCT/IL2010/000193.
Windisch et al. "§-Synuclein-Derived Peptides With Neuroprotective Activity. An Alternative Treatment of Neurodegenerative Activity?", Journal of Molecular Neuroscience, 24: 155-165, 2004.
Windisch et al. "Development of a New Treatment for Alzheimer's Disease and Parkinson's Disease Using Anti-Aggregatory §-Synuclein-Derived Peptides", Journal of Molecular Neuroscience, 19: 63-69, 2002.
International Preliminary Report on Patentability Dated Sep. 22, 2011 From the International Bureau of WIPO Re. Application No. PCT/IL2010/000193.
Communication Pursuant to Article 94(3) EPC Dated May 10, 2013 From the European Patent Office Re. Application No. 10714094.9.
Translation of Notification of the Office Action Dated May 6, 2013 From the State Intellectual Property Office of the People's Republic of China Re. Application No. 201080011343.8.
Translation of Search Report Dated May 6, 2013 From the State Intellectual Property Office of the People's Republic of China Re. Application No. 201080011343.8.

*Primary Examiner* — Gregory S Emch

(57) ABSTRACT

Isolated peptides are provided, being less than 20 amino acids in length. The peptides comprising an amino acid sequence GVLYVGSKTREGV (SEQ ID NO: 12) AAATGLVKREE (SEQ ID NO: 13) or GVVAAAEKTKQG (SEQ ID NO: 14), mimetics and/or fragment thereof, the peptides being capable of inhibiting alpha synuclein aggregation. Pharmaceutical compositions comprising same are also provided as well as uses thereof.

13 Claims, 10 Drawing Sheets

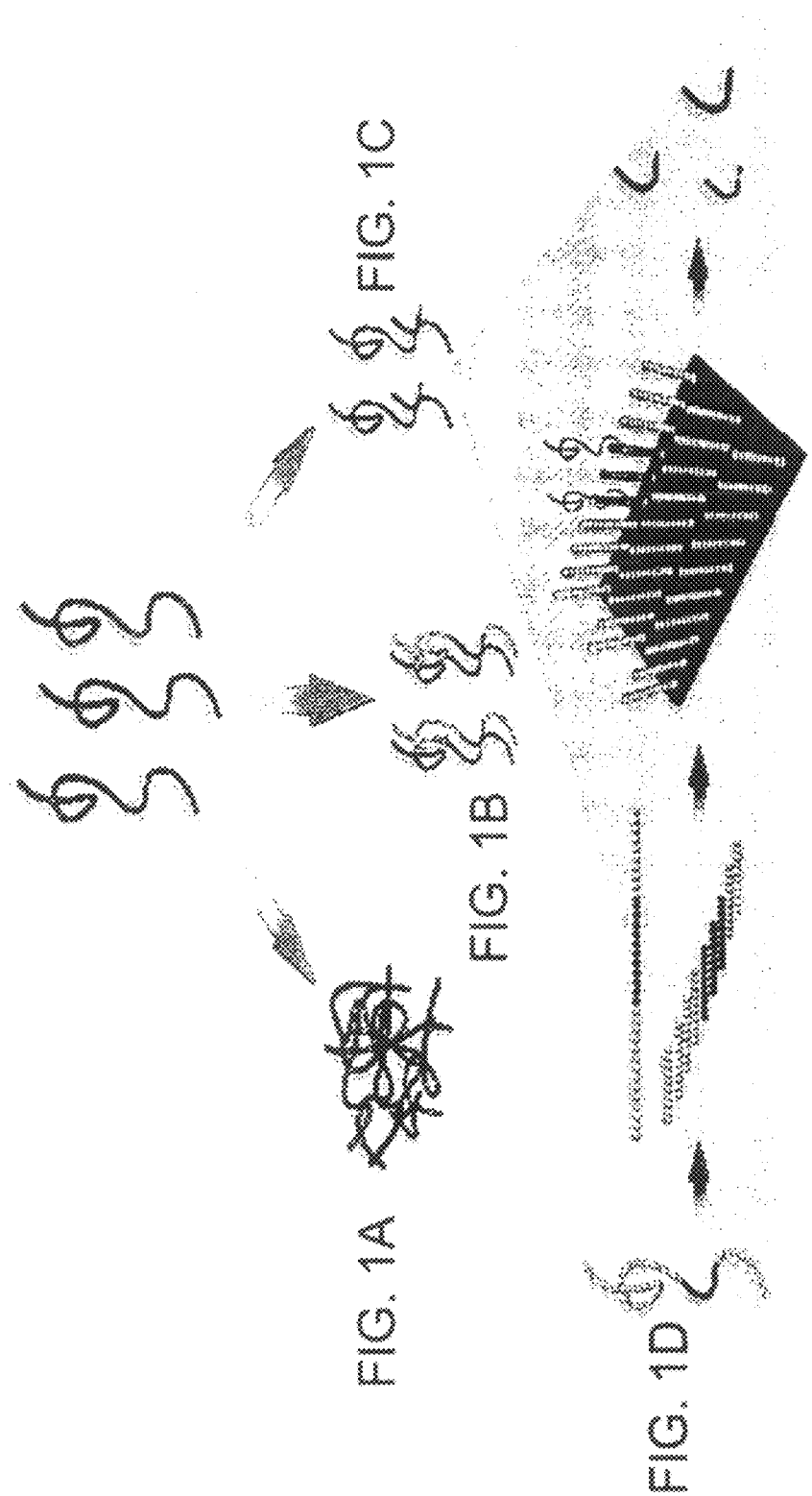

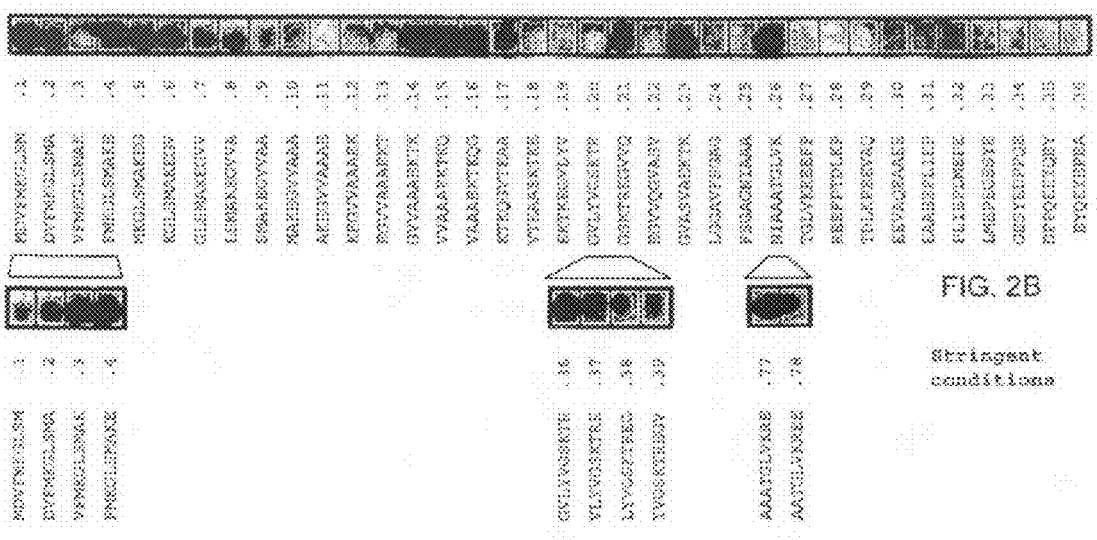

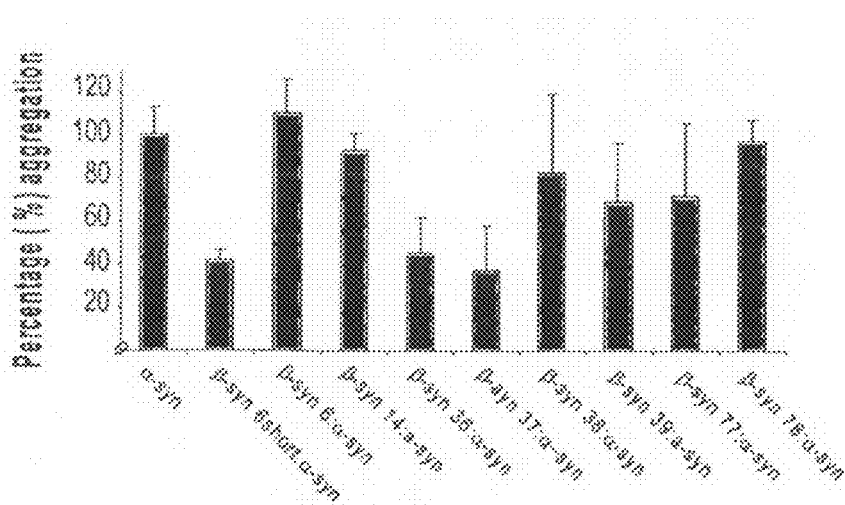
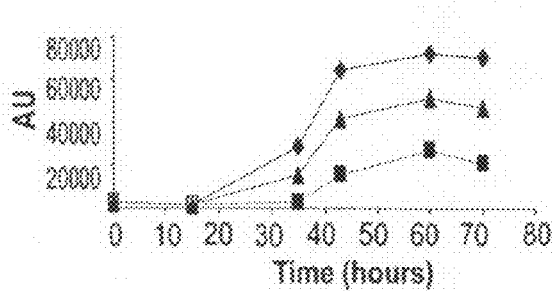 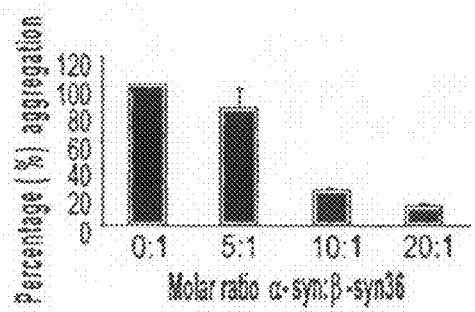
FIG. 3A
FIG. 3B  FIG. 3C
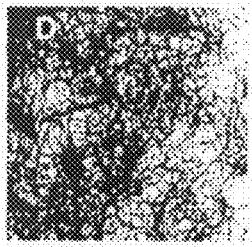 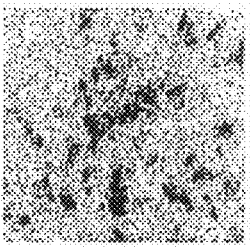 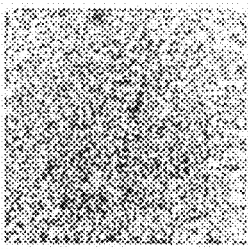 
FIG. 3D  FIG. 3E  FIG. 3F  FIG. 3G
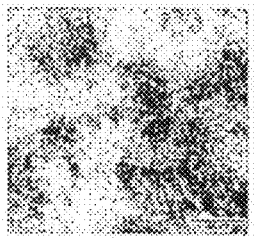 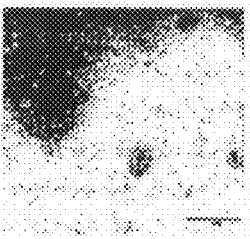 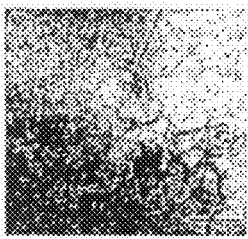 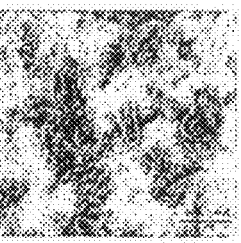
FIG. 3H  FIG. 3I  FIG. 3J  FIG. 3K

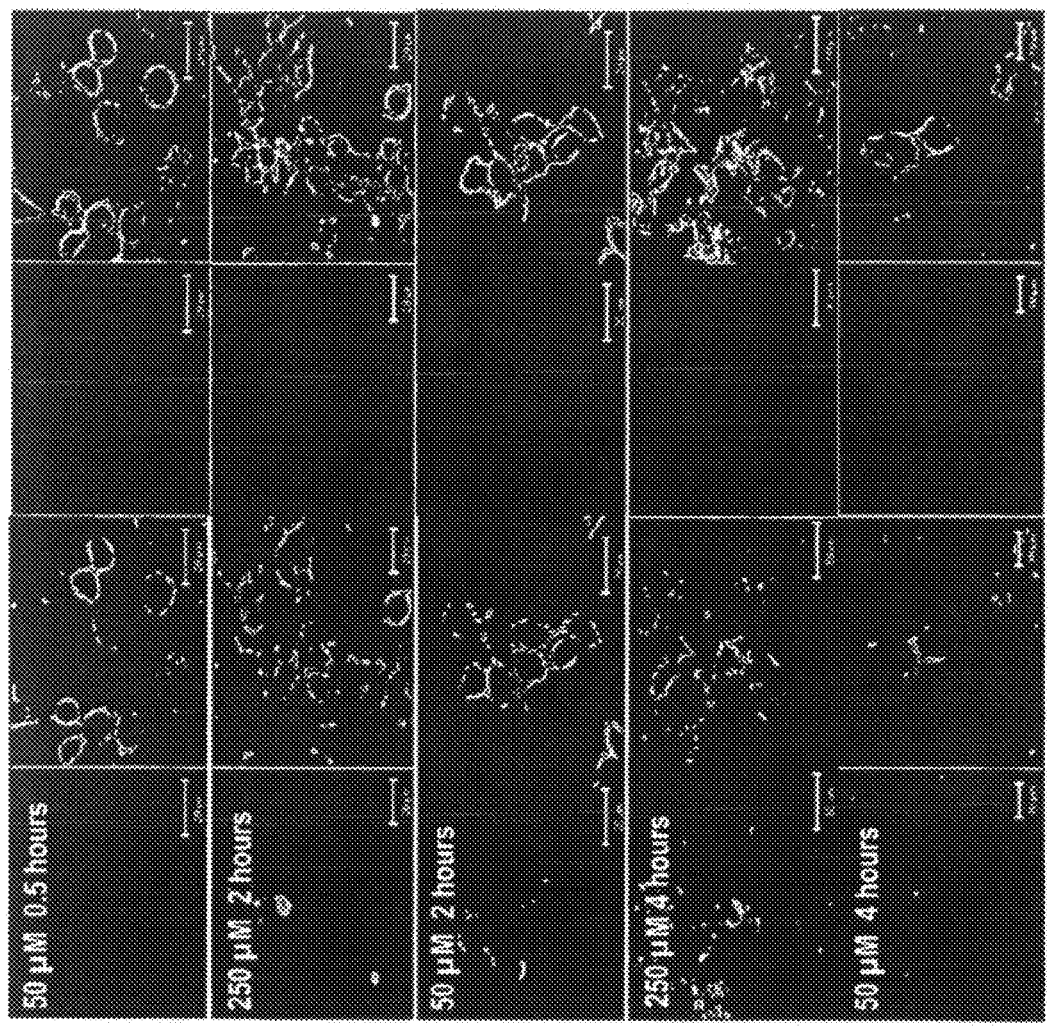

SEQUENCE LISTING

<160> NUMBER OF SEQ ID NOS: 60

<210> SEQ ID NO 1
<211> LENGTH: 10
<212> TYPE: PRT
<213> ORGANISM: Artificial sequence
<220> FEATURE:
<223> OTHER INFORMATION: Synthetic peptide

<400> SEQUENCE: 1

Gly Val Leu Tyr Val Gly Ser Lys Thr Arg
1               5                   10

```
<210> SEQ ID NO 2
<211> LENGTH: 10
<212> TYPE: PRT
<213> ORGANISM: Artificial sequence
<220> FEATURE:
<223> OTHER INFORMATION: Synthetic peptide

<400> SEQUENCE: 2

Val Leu Tyr Val Gly Ser Lys Thr Arg Glu
1               5                   10

<210> SEQ ID NO 3
<211> LENGTH: 10
<212> TYPE: PRT
<213> ORGANISM: Artificial sequence
<220> FEATURE:
<223> OTHER INFORMATION: Synthetic peptide

<400> SEQUENCE: 3

Leu Tyr Val Gly Ser Lys Thr Arg Glu Gly
1               5                   10

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Tyr Val Gly Ser Lys Thr Arg Glu Gly Val
1               5                   10

<210> SEQ ID NO 5
<211> LENGTH: 10
<212> TYPE: PRT
<213> ORGANISM: Artificial sequence
<220> FEATURE:
<223> OTHER INFORMATION: Synthetic peptide

<400> SEQUENCE: 5

Ala Ala Ala Thr Gly Leu Val Lys Arg Glu
1               5                   10

<210> SEQ ID NO 6
<211> LENGTH: 10
<212> TYPE: PRT
<213> ORGANISM: Artificial sequence
<220> FEATURE:
<223> OTHER INFORMATION: Synthetic peptide

<400> SEQUENCE: 6

Ala Ala Thr Gly Leu Val Lys Arg Glu Glu
1               5                   10

<210> SEQ ID NO 7
<211> LENGTH: 10
<212> TYPE: PRT
<213> ORGANISM: Artificial sequence
<220> FEATURE:
<223> OTHER INFORMATION: Synthetic peptide

<400> SEQUENCE: 7

Gly Val Ala Ser Val Ala Glu Lys Thr Lys
1               5                   10
```

```
<210> SEQ ID NO 8
<211> LENGTH: 10
<212> TYPE: PRT
<213> ORGANISM: Artificial sequence
<220> FEATURE:
<223> OTHER INFORMATION: Synthetic peptide

<400> SEQUENCE: 8

Gly Val Val Ala Ala Ala Glu Lys Thr Lys
1               5                   10

<210> SEQ ID NO 9
<211> LENGTH: 10
<212> TYPE: PRT
<213> ORGANISM: Artificial sequence
<220> FEATURE:
<223> OTHER INFORMATION: Synthetic peptide

<400> SEQUENCE: 9

Val Val Ala Ala Ala Glu Lys Thr Lys Gln
1               5                   10

<210> SEQ ID NO 10
<211> LENGTH: 10
<212> TYPE: PRT
<213> ORGANISM: Artificial sequence
<220> FEATURE:
<223> OTHER INFORMATION: Synthetic peptide

<400> SEQUENCE: 10

Val Ala Ala Ala Glu Lys Thr Lys Gln Gly
1               5                   10

<210> SEQ ID NO 11
<211> LENGTH: 10
<212> TYPE: PRT
<213> ORGANISM: Artificial sequence
<220> FEATURE:
<223> OTHER INFORMATION: Synthetic peptide

<400> SEQUENCE: 11

Leu Gly Gly Ala Val Phe Ser Gly Ala Gly
1               5                   10

<210> SEQ ID NO 12
<211> LENGTH: 13
<212> TYPE: PRT
<213> ORGANISM: Artificial sequence
<220> FEATURE:
<223> OTHER INFORMATION: Synthetic peptide

<400> SEQUENCE: 12

Gly Val Leu Tyr Val Gly Ser Lys Thr Arg Glu Gly Val
1               5                   10

<210> SEQ ID NO 13
<211> LENGTH: 11
<212> TYPE: PRT
<213> ORGANISM: Artificial sequence
<220> FEATURE:
<223> OTHER INFORMATION: Synthetic peptide

<400> SEQUENCE: 13

Ala Ala Ala Thr Gly Leu Val Lys Arg Glu Glu
1               5                   10
```

```
<210> SEQ ID NO 14
<211> LENGTH: 12
<212> TYPE: PRT
<213> ORGANISM: Artificial sequence
<220> FEATURE:
<223> OTHER INFORMATION: Synthetic peptide

<400> SEQUENCE: 14

Gly Val Val Ala Ala Glu Lys Thr Lys Gln Gly
1               5                   10

<210> SEQ ID NO 15
<211> LENGTH: 134
<212> TYPE: PRT
<213> ORGANISM: Homo sapiens

<400> SEQUENCE: 15

Met Asp Val Phe Met Lys Gly Leu Ser Met Ala Lys Glu Gly Val Val
1               5                   10                  15

Ala Ala Ala Glu Lys Thr Lys Gln Gly Val Thr Glu Ala Ala Glu Lys
            20                  25                  30

Thr Lys Glu Gly Val Leu Tyr Val Gly Ser Lys Thr Arg Glu Gly Val
        35                  40                  45

Val Gln Gly Val Ala Ser Val Ala Glu Lys Thr Lys Glu Gln Ala Ser
    50                  55                  60

His Leu Gly Gly Ala Val Phe Ser Gly Ala Gly Asn Ile Ala Ala Ala
65                  70                  75                  80

Thr Gly Leu Val Lys Arg Glu Glu Phe Pro Thr Asp Leu Lys Pro Glu
                85                  90                  95

Glu Val Ala Gln Glu Ala Ala Glu Glu Pro Leu Ile Glu Pro Leu Met
            100                 105                 110

Glu Pro Glu Gly Glu Ser Tyr Glu Asp Pro Pro Gln Glu Glu Tyr Gln
        115                 120                 125

Glu Tyr Glu Pro Glu Ala
    130

<210> SEQ ID NO 16
<211> LENGTH: 134
<212> TYPE: PRT
<213> ORGANISM: Homo sapiens

<400> SEQUENCE: 16

Met Asp Val Phe Met Lys Gly Leu Ser Met Ala Lys Glu Gly Val Val
1               5                   10                  15

Ala Ala Ala Glu Lys Thr Lys Gln Gly Val Thr Glu Ala Ala Glu Lys
            20                  25                  30

Thr Lys Glu Gly Val Leu Tyr Val Gly Ser Lys Thr Arg Glu Gly Val
        35                  40                  45

Val Gln Gly Val Ala Ser Val Ala Glu Lys Thr Lys Glu Gln Ala Ser
    50                  55                  60

His Leu Gly Gly Ala Val Phe Ser Gly Ala Gly Asn Ile Ala Ala Ala
65                  70                  75                  80

Thr Gly Leu Val Lys Arg Glu Glu Phe Pro Thr Asp Leu Lys Pro Glu
                85                  90                  95

Glu Val Ala Gln Glu Ala Ala Glu Glu Pro Leu Ile Glu Pro Leu Met
            100                 105                 110
```

```
Glu Pro Glu Gly Glu Ser Tyr Glu Asp Pro Pro Gln Glu Glu Tyr Gln
        115                 120                 125

Glu Tyr Glu Pro Glu Ala
    130

<210> SEQ ID NO 17
<211> LENGTH: 11
<212> TYPE: PRT
<213> ORGANISM: Artificial sequence
<220> FEATURE:
<223> OTHER INFORMATION: Synthetic peptide

<400> SEQUENCE: 17

Tyr Val Gly Ser Lys Thr Arg Glu Gly Val Val
1               5                   10

<210> SEQ ID NO 18
<211> LENGTH: 11
<212> TYPE: PRT
<213> ORGANISM: Artificial sequence
<220> FEATURE:
<223> OTHER INFORMATION: Synthetic peptide

<400> SEQUENCE: 18

Val Ala Ala Ala Glu Lys Thr Lys Gln Gly Val
1               5                   10

<210> SEQ ID NO 19
<211> LENGTH: 2
<212> TYPE: PRT
<213> ORGANISM: Artificial sequence
<220> FEATURE:
<223> OTHER INFORMATION: Synthetic peptide

<400> SEQUENCE: 19

Leu Ser
1

<210> SEQ ID NO 20
<211> LENGTH: 2
<212> TYPE: PRT
<213> ORGANISM: Artificial sequence
<220> FEATURE:
<223> OTHER INFORMATION: Synthetic peptide

<400> SEQUENCE: 20

Gly Leu
1

<210> SEQ ID NO 21
<211> LENGTH: 3
<212> TYPE: PRT
<213> ORGANISM: Artificial sequence
<220> FEATURE:
<223> OTHER INFORMATION: Synthetic peptide

<400> SEQUENCE: 21

Lys Glu Gly
1

<210> SEQ ID NO 22
<211> LENGTH: 10
<212> TYPE: PRT
<213> ORGANISM: Artificial sequence
<220> FEATURE:
<223> OTHER INFORMATION: Synthetic peptide
```

```
<400> SEQUENCE: 22

Gly Val Leu Trp Val Gly Ser Lys Thr Arg
1               5                   10

<210> SEQ ID NO 23
<211> LENGTH: 10
<212> TYPE: PRT
<213> ORGANISM: Artificial sequence
<220> FEATURE:
<223> OTHER INFORMATION: Synthetic peptide

<400> SEQUENCE: 23

Met Asp Val Phe Met Lys Gly Leu Ser Met
1               5                   10

<210> SEQ ID NO 24
<211> LENGTH: 10
<212> TYPE: PRT
<213> ORGANISM: Artificial sequence
<220> FEATURE:
<223> OTHER INFORMATION: Synthetic peptide

<400> SEQUENCE: 24

Asp Val Phe Met Lys Gly Leu Ser Met Ala
1               5                   10

<210> SEQ ID NO 25
<211> LENGTH: 10
<212> TYPE: PRT
<213> ORGANISM: Artificial sequence
<220> FEATURE:
<223> OTHER INFORMATION: Synthetic peptide

<400> SEQUENCE: 25

Val Phe Met Lys Gly Leu Ser Met Ala Lys
1               5                   10

<210> SEQ ID NO 26
<211> LENGTH: 10
<212> TYPE: PRT
<213> ORGANISM: Artificial sequence
<220> FEATURE:
<223> OTHER INFORMATION: Synthetic peptide

<400> SEQUENCE: 26

Phe Met Lys Gly Leu Ser Met Ala Lys Glu
1               5                   10

<210> SEQ ID NO 27
<211> LENGTH: 10
<212> TYPE: PRT
<213> ORGANISM: Artificial sequence
<220> FEATURE:
<223> OTHER INFORMATION: Synthetic peptide

<400> SEQUENCE: 27

Met Lys Gly Leu Ser Met Ala Lys Glu Gly
1               5                   10

<210> SEQ ID NO 28
<211> LENGTH: 10
<212> TYPE: PRT
<213> ORGANISM: Artificial sequence
<220> FEATURE:
<223> OTHER INFORMATION: Synthetic peptide
```

-continued

```
<400> SEQUENCE: 28

Lys Gly Leu Ser Met Ala Lys Glu Gly Val
1               5                   10

<210> SEQ ID NO 29
<211> LENGTH: 10
<212> TYPE: PRT
<213> ORGANISM: Artificial sequence
<220> FEATURE:
<223> OTHER INFORMATION: Synthetic peptide

<400> SEQUENCE: 29

Gly Leu Ser Met Ala Lys Glu Gly Val Val
1               5                   10

<210> SEQ ID NO 30
<211> LENGTH: 10
<212> TYPE: PRT
<213> ORGANISM: Artificial sequence
<220> FEATURE:
<223> OTHER INFORMATION: Synthetic peptide

<400> SEQUENCE: 30

Leu Ser Met Ala Lys Glu Gly Val Val Ala
1               5                   10

<210> SEQ ID NO 31
<211> LENGTH: 10
<212> TYPE: PRT
<213> ORGANISM: Artificial sequence
<220> FEATURE:
<223> OTHER INFORMATION: Synthetic peptide

<400> SEQUENCE: 31

Ser Met Ala Lys Glu Gly Val Val Ala Ala
1               5                   10

<210> SEQ ID NO 32
<211> LENGTH: 10
<212> TYPE: PRT
<213> ORGANISM: Artificial sequence
<220> FEATURE:
<223> OTHER INFORMATION: Synthetic peptide

<400> SEQUENCE: 32

Met Ala Lys Glu Gly Val Val Ala Ala Ala
1               5                   10

<210> SEQ ID NO 33
<211> LENGTH: 10
<212> TYPE: PRT
<213> ORGANISM: Artificial sequence
<220> FEATURE:
<223> OTHER INFORMATION: Synthetic peptide

<400> SEQUENCE: 33

Ala Lys Glu Gly Val Val Ala Ala Ala Glu
1               5                   10

<210> SEQ ID NO 34
<211> LENGTH: 10
<212> TYPE: PRT
<213> ORGANISM: Artificial sequence
<220> FEATURE:
<223> OTHER INFORMATION: Synthetic peptide
```

```
<400> SEQUENCE: 34

Lys Glu Gly Val Val Ala Ala Ala Glu Lys
1               5                   10

<210> SEQ ID NO 35
<211> LENGTH: 10
<212> TYPE: PRT
<213> ORGANISM: Artificial sequence
<220> FEATURE:
<223> OTHER INFORMATION: Synthetic peptide

<400> SEQUENCE: 35

Glu Gly Val Val Ala Ala Ala Glu Lys Thr
1               5                   10

<210> SEQ ID NO 36
<211> LENGTH: 10
<212> TYPE: PRT
<213> ORGANISM: Artificial sequence
<220> FEATURE:
<223> OTHER INFORMATION: Synthetic peptide

<400> SEQUENCE: 36

Lys Thr Lys Gln Gly Val Thr Glu Ala Ala
1               5                   10

<210> SEQ ID NO 37
<211> LENGTH: 10
<212> TYPE: PRT
<213> ORGANISM: Artificial sequence
<220> FEATURE:
<223> OTHER INFORMATION: Synthetic peptide

<400> SEQUENCE: 37

Val Thr Glu Ala Ala Glu Lys Thr Lys Glu
1               5                   10

<210> SEQ ID NO 38
<211> LENGTH: 10
<212> TYPE: PRT
<213> ORGANISM: Artificial sequence
<220> FEATURE:
<223> OTHER INFORMATION: Synthetic peptide

<400> SEQUENCE: 38

Glu Lys Thr Lys Glu Gly Val Leu Tyr Val
1               5                   10

<210> SEQ ID NO 39
<211> LENGTH: 7
<212> TYPE: PRT
<213> ORGANISM: Artificial sequence
<220> FEATURE:
<223> OTHER INFORMATION: Synthetic peptide

<400> SEQUENCE: 39

Ser Met Ala Lys Glu Gly Val
1               5

<210> SEQ ID NO 40
<211> LENGTH: 10
<212> TYPE: PRT
<213> ORGANISM: Artificial sequence
<220> FEATURE:
<223> OTHER INFORMATION: Synthetic peptide
```

```
<400> SEQUENCE: 40

Gly Ser Lys Thr Arg Glu Gly Val Val Gln
1               5                   10

<210> SEQ ID NO 41
<211> LENGTH: 10
<212> TYPE: PRT
<213> ORGANISM: Artificial sequence
<220> FEATURE:
<223> OTHER INFORMATION: Synthetic peptide

<400> SEQUENCE: 41

Glu Gly Val Val Gln Gly Val Ala Ser Val
1               5                   10

<210> SEQ ID NO 42
<211> LENGTH: 10
<212> TYPE: PRT
<213> ORGANISM: Artificial sequence
<220> FEATURE:
<223> OTHER INFORMATION: Synthetic peptide

<400> SEQUENCE: 42

Phe Ser Gly Ala Gly Asn Ile Ala Ala Ala
1               5                   10

<210> SEQ ID NO 43
<211> LENGTH: 10
<212> TYPE: PRT
<213> ORGANISM: Artificial sequence
<220> FEATURE:
<223> OTHER INFORMATION: Synthetic peptide

<400> SEQUENCE: 43

Asn Ile Ala Ala Ala Thr Gly Leu Val Lys
1               5                   10

<210> SEQ ID NO 44
<211> LENGTH: 10
<212> TYPE: PRT
<213> ORGANISM: Artificial sequence
<220> FEATURE:
<223> OTHER INFORMATION: Synthetic peptide

<400> SEQUENCE: 44

Thr Gly Leu Val Lys Arg Glu Glu Phe Pro
1               5                   10

<210> SEQ ID NO 45
<211> LENGTH: 10
<212> TYPE: PRT
<213> ORGANISM: Artificial sequence
<220> FEATURE:
<223> OTHER INFORMATION: Synthetic peptide

<400> SEQUENCE: 45

Arg Glu Glu Phe Pro Thr Asp Leu Lys Pro
1               5                   10

<210> SEQ ID NO 46
<211> LENGTH: 10
<212> TYPE: PRT
<213> ORGANISM: Artificial sequence
<220> FEATURE:
<223> OTHER INFORMATION: Synthetic peptide
```

```
<400> SEQUENCE: 46

Thr Asp Leu Lys Pro Glu Glu Val Ala Gln
1               5                   10

<210> SEQ ID NO 47
<211> LENGTH: 10
<212> TYPE: PRT
<213> ORGANISM: Artificial sequence
<220> FEATURE:
<223> OTHER INFORMATION: Synthetic peptide

<400> SEQUENCE: 47

Glu Glu Val Ala Gln Glu Ala Ala Glu Glu
1               5                   10

<210> SEQ ID NO 48
<211> LENGTH: 10
<212> TYPE: PRT
<213> ORGANISM: Artificial sequence
<220> FEATURE:
<223> OTHER INFORMATION: Synthetic peptide

<400> SEQUENCE: 48

Glu Ala Ala Glu Glu Pro Leu Ile Glu Pro
1               5                   10

<210> SEQ ID NO 49
<211> LENGTH: 10
<212> TYPE: PRT
<213> ORGANISM: Artificial sequence
<220> FEATURE:
<223> OTHER INFORMATION: Synthetic peptide

<400> SEQUENCE: 49

Pro Leu Ile Glu Pro Leu Met Glu Pro Glu
1               5                   10

<210> SEQ ID NO 50
<211> LENGTH: 10
<212> TYPE: PRT
<213> ORGANISM: Artificial sequence
<220> FEATURE:
<223> OTHER INFORMATION: Synthetic peptide

<400> SEQUENCE: 50

Leu Met Glu Pro Glu Gly Glu Ser Tyr Glu
1               5                   10

<210> SEQ ID NO 51
<211> LENGTH: 10
<212> TYPE: PRT
<213> ORGANISM: Artificial sequence
<220> FEATURE:
<223> OTHER INFORMATION: Synthetic peptide

<400> SEQUENCE: 51

Gly Glu Ser Tyr Glu Asp Pro Pro Gln Glu
1               5                   10

<210> SEQ ID NO 52
<211> LENGTH: 10
<212> TYPE: PRT
<213> ORGANISM: Artificial sequence
<220> FEATURE:
<223> OTHER INFORMATION: Synthetic peptide
```

-continued

```
<400> SEQUENCE: 52

Asp Pro Pro Gln Glu Glu Tyr Gln Glu Tyr
1               5                   10

<210> SEQ ID NO 53
<211> LENGTH: 9
<212> TYPE: PRT
<213> ORGANISM: Artificial sequence
<220> FEATURE:
<223> OTHER INFORMATION: Synthetic peptide

<400> SEQUENCE: 53

Glu Tyr Gln Glu Tyr Glu Pro Glu Ala
1               5

<210> SEQ ID NO 54
<211> LENGTH: 10
<212> TYPE: PRT
<213> ORGANISM: Artificial sequence
<220> FEATURE:
<223> OTHER INFORMATION: Synthetic peptide

<400> SEQUENCE: 54

Gly Val Leu Tyr Val Gly Ser Lys Thr Arg
1               5                   10

<210> SEQ ID NO 55
<211> LENGTH: 10
<212> TYPE: PRT
<213> ORGANISM: Artificial sequence
<220> FEATURE:
<223> OTHER INFORMATION: Synthetic peptide

<400> SEQUENCE: 55

Arg Thr Lys Ser Gly Val Tyr Leu Val Gly
1               5                   10

<210> SEQ ID NO 56
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' acetylated peptide
<220> FEATURE:
<221> NAME/KEY: misc_feature
<222> LOCATION: (10)..(10)
<223> OTHER INFORMATION: C' amide

<400> SEQUENCE: 56

Arg Thr Lys Ser Gly Val Tyr Leu Val Gly
1               5                   10

<210> SEQ ID NO 57
<211> LENGTH: 7
<212> TYPE: PRT
<213> ORGANISM: Artificial sequence
<220> FEATURE:
<223> OTHER INFORMATION: Synthetic peptide

<400> SEQUENCE: 57

Tyr Val Gly Ser Lys Thr Arg
1               5
```

```
<210> SEQ ID NO 58
<211> LENGTH: 3
<212> TYPE: PRT
<213> ORGANISM: Artificial sequence
<220> FEATURE:
<223> OTHER INFORMATION: Synthetic peptide

<400> SEQUENCE: 58

Lys Thr Arg
1

<210> SEQ ID NO 59
<211> LENGTH: 4
<212> TYPE: PRT
<213> ORGANISM: Artificial sequence
<220> FEATURE:
<223> OTHER INFORMATION: Synthetic peptide

<400> SEQUENCE: 59

Lys Thr Arg Glu
1

<210> SEQ ID NO 60
<211> LENGTH: 4
<212> TYPE: PRT
<213> ORGANISM: Artificial sequence
<220> FEATURE:
<223> OTHER INFORMATION: Synthetic peptide

<400> SEQUENCE: 60

Lys Thr Arg Gly
1
```

COMPOSITIONS AND METHODS FOR TREATMENT OF NEURODEGENERATIVE DISEASES

RELATED APPLICATIONS

This application is a National Phase of PCT Patent Application No. PCT/IL2010/000193 having International filing date of Mar. 9, 2010, which claims the benefit of priority of U.S. Provisional Patent Application No. 61/202,523 filed on Mar. 9, 2009. The contents of the above applications are all incorporated herein by reference.

FIELD AND BACKGROUND OF THE INVENTION

Many diseases are caused by inherited or acquired modifications of proteins and polypeptides' structure. Conformational diseases arise when a constituent protein undergoes a change in size or fluctuation in shape with resultant self-association and tissue deposition, such as amyloid fibrils.

The role of protein deposition in neurodegenerative diseases has become evident in a large group of etiologically diverse diseases including Alzheimer's disease, Huntington's disease, Parkinson's disease, Creutzfeldt-Jacob disease, prion disorders and Type II diabetes. In each of the various diseases, a different endogenous protein self-assembles into highly ordered fibrillar structure. Though there is no specific sequence homology between the proteins associated with each one of these diseases, they are all thought to involve important conformational changes in proteins, usually produce β-sheet structures with a strong tendency to aggregate into water-insoluble fibrous polymers.

Parkinson's disease (PD), the second most common form of neurodegenerative diseases after Alzheimer's disease, is a devastating neurological disease without cure, affecting 1-2% of the elderly population. The neuropathological hallmarks are characterized by progressive and profound loss of neuromelanin containing dopaminergic neurons in the substantia nigra pars compacta with presence of eosinophillic, intracytoplamic, proteinaceous inclusions termed as Lewy bodies (LB) and dystrophic Lewy neuritis (LN) in surviving neurons. Among the clinical features of PD are motor impairments involving resting tremor, bradykinesia, postural instability and rigidity along with non-motoric symptoms like autonomic, cognitive and psychiatric problems. The cause of these pathological characteristics is not yet fully understood but it is believed that environmental factors as well as a genetic causation or a combination of the two might result in the abovementioned clinical syndromes. It is now known that less than 10% of the PD cases has a strict familial etiology while the majority of cases are sporadic. Among the mutations associated with familial PD, three missense mutations in the α-synuclein (α-syn) gene termed A53T, A30P and E46K have been widely characterized [Lotharius, J., and Brundin, P. (2002) Nat Rev Neurosci 3(12), 932-942].

The α-syn protein is composed of 140 amino acid residues. It is a small, highly charged, natively-unfolded protein. It was first identified as the major component of LB and LN. α-syn can be divided into three major regions: the amino terminal region containing several imperfect repeats of the sequence KTKEGV, a hydrophobic central domain called the non-amyloid component (NAC) region and the carboxy terminal characterized by its highly negatively charged amino acids. It is predominantly expressed in central nervous system (CNS) neurons, where it is localized at presynaptic terminals in close proximity to synaptic vesicles and can associate with lipid membranes by forming amphipathic α-helices.

α-syn is a family member of the synuclein proteins, along with beta synuclein (β-syn) and gamma synuclein (γ-syn). α-syn and β-syn are found primarily in brain tissues, located mainly in the pre-synaptic nerve terminals while γ-syn is primarily found in the peripheral nervous system and the retina, although it has also been found to be highly expressed in some tumor tissues, including breast, ovarian and bladder tissues.

The sequence of the three synucleins is highly conserved, especially within their N terminal domain. When comparing the sequences of α-syn and β-syn, there is a major difference within the hydrophobic central domain; β-syn, a 134 amino acids protein, is missing the NAC region of α-syn and does not aggregate to form amyloid fibrils during different stress conditions, such as free radicals or increased concentration.

In the case of various neurodegenerative diseases, an alteration of the quantitative ratio between the individual synucleins occurs to the extent that the relative proportion of alpha-synuclein is increased. It was possible to detect in vitro that beta-synuclein is able to inhibit the aggregation of alpha-synuclein in a dose-dependent manner (Hashimoto et al., Neuron 32 (2): 213-23 [2001]). Tests in cell cultures in which a disruption of the normal cell proliferation and differentiation was triggered by over-expression of alpha-synuclein also showed an advantageous action, in the therapeutic sense, of beta-synuclein, which further normalized the adhesion, survival and growth of neurites in these cultures. Mice, which are transgenic for alpha-synuclein, show an elevated production of this albumin and therefore exhibit a disrupted ratio in the amounts between alpha- and beta-synuclein. Over the course of aging, they form intraneuronal inclusion bodies that are similar to Lewy Bodies and also show progressive motor disruptions, which are comparable to the disruption of function in Parkinson's disease. If these animals with alpha-synuclein are crossed with beta-synuclein transgenic mice, which show an elevated expression of this albumin, a significantly higher level in the overall expression of the synucleins can restore a homoeostasis. As a result, the number of inclusion bodies is highly significantly reduced, and the characteristic neuronal function loss is completely prevented.

Alpha-synuclein is believed to play an especially important role in the pathology of Alzheimer's disease. This is indicated by the fact that a portion of this protein, the NACP (Non-Amyloid Component Protein) domain, could be demonstrated as part of the senile plaques (Yoshimoto et al., Proc. Natl. Acad Sci 92, 9141-5 [1995] and WO-9506407), in addition to the fact that about 70% of patients suffering from Alzheimer's disease exhibit Lewy Bodies in various areas of the brain, in which alpha-synuclein is also found (Eizo et al., Neurosci. Lett. 290 (1), 41-4 [2000]). In a transgenic mouse model, beta-amyloid increases the accumulation and the neurotoxicity of alpha-synuclein (Masliah et al., Proc. Natl. Acad. Sci. 98 (21): 12245-50 [2001]).

Beta-synuclein and in particular peptides derived therefrom for disruption of alpha-synucleic aggregates have been described. See for example, octapeptides according to WO/02/04482 and three additional peptides in WO02/04625. WO002/0020 and WO01/60794 describe the use of beta-synuclein as a whole molecule or methods that increase its expression in vivo for therapy of neurological diseases that are associated with alpha-synuclein. WO-A-01/60794 in particular also teaches the use of a peptide which corresponds to the N-terminal amino acids 1 to 15 of the beta-synuclein, for preventing the aggregation of alpha-synuclein and beta-amyloid. Likewise US2006/0036073 and US20080200397 teach shorter peptide fragments derived from the N-terminal amino acids 1 to 15 of the beta-synuclein, for preventing the binding of alpha-synuclein and beta-amyloid. U.S. 20010047032 teach aromatic compounds for the treatment of amyloidosis and alpha-synuclein fibril diseases. Windisch et al teach experiments with deletion mutants of β-syn which focused on the N-terminal amino acids 1-15 of the protein. They created a peptide library containing different variations of amino acid composition derived from this sequence of β-syn, with the specific aim of finding a peptide that can be used for therapeutic application immediately or can serve as a basis for developing peptidomimetic small molecules (Windisch et al., 2004, J Mol Neurosci 24(1), 155-165).

SUMMARY OF THE INVENTION

According to an aspect of some embodiments of the present invention there is provided an isolated peptide being less than 20 amino acids in length, the peptide comprising an amino acid sequence GVLYVGSKTREGV (SEQ ID NO: 12) AAATGLVKREE (SEQ ID NO: 13) or GVVAAAEKTKQG (SEQ ID NO: 14), mimetics and/or fragment thereof, the peptide being capable of inhibiting alpha synuclein aggregation.

According to an aspect of some embodiments of the present invention there is provided a pharmaceutical composition comprising as an active ingredient the peptide of the present invention and a pharmaceutically acceptable carrier.

According to an aspect of some embodiments of the present invention there is provided a method of inhibiting alpha-synuclein aggregation, the method comprising contacting alpha-synuclein with the peptide of the present invention, thereby inhibiting alpha-synuclein aggregation.

According to an aspect of some embodiments of the present invention there is provided a method of treating or preventing a medical condition associated with alpha-synuclein aggregation, the method comprising administering to a subject in need thereof a therapeutically effective amount of the peptide of the present invention, thereby treating the medical condition associated with alpha-synuclein aggregation.

According to an aspect of some embodiments of the present invention there is provided a method of detecting alpha-synuclein monomers, the method comprising:

(a) contacting a biological sample selected suspected of comprising the alpha-synuclein monomers with the peptide of the present invention under conditions which allow complex formation between the monomers and the peptide; and (b) detecting presence or level of the complex, thereby detecting alpha-synuclein monomers.

According to some embodiments of the invention, the peptide comprises at least one aromatic amino acid.

According to some embodiments of the invention, the peptide comprises at least one basic amino acid.

According to some embodiments of the invention, the peptide comprises at least one beta-breaker amino acid.

According to some embodiments of the invention, the beta-breaker amino acid is a synthetic amino acid.

According to some embodiments of the invention, the beta-breaker amino acid is naturally occurring.

According to some embodiments of the invention, the amino acid sequence comprises at least one D-amino acid residue.

According to some embodiments of the invention, the peptide has an end cap modification.

According to some embodiments of the invention, the peptide comprises KTR or mimetics thereof.

According to some embodiments of the invention, the peptide comprises KTRE or mimetics thereof.

According to some embodiments of the invention, the peptide comprises KTREG or mimetics thereof.

According to some embodiments of the invention, the peptide is selected from the group consisting of SEQ ID NOs: 1, 2, 3, 4, 8, 9, 10, 12 and 13.

According to some embodiments of the invention, the peptide is selected from the group consisting of SEQ ID NOs: 5 and 6.

According to some embodiments of the invention, the peptide is selected from the group consisting of SEQ ID NOs: 1, 2, 3 and 4.

According to some embodiments of the invention, the medical condition is selected from the group consisting of Parkinson's disease (PD), Alzheimer's disease (AD), diffuse Lewy body disease, mixed AD-PD, multiple system atrophy and Hallervorden-Spatz disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figures 4A, 4B:
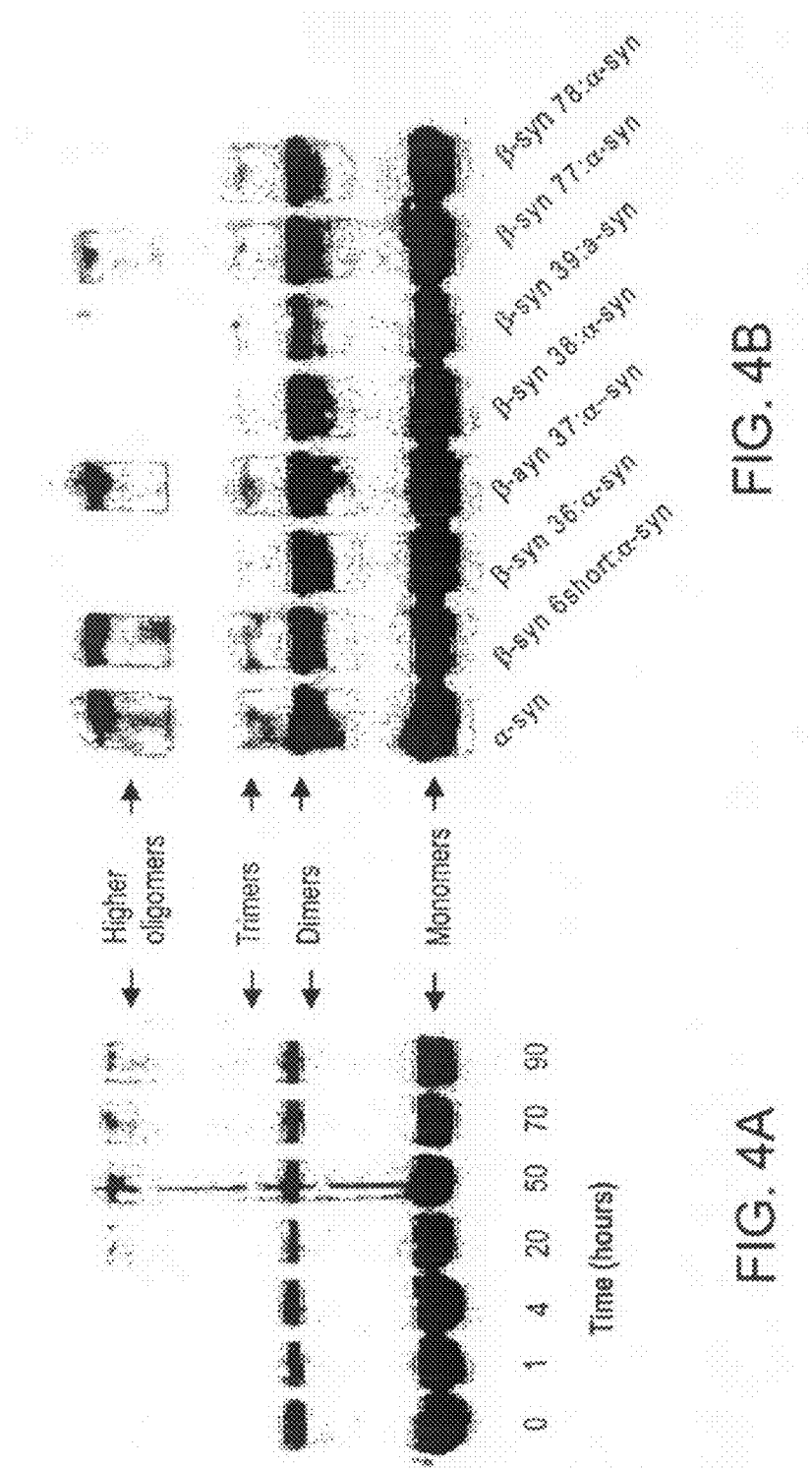

FIGS. 1A-D are schematic illustrations of β derived peptides as inhibitors of α-syn aggregation. FIG. 1A. β-syn inhibits the formation of α-syn aggregates. FIG. 1B. Molecular mapping of β-syn binding sequences to α-syn using peptide-array analysis. FIG. 1C. Potential peptide based inhibitors for α-syn aggregation. FIG. 1D. Schematic illustration of the peptide array technique (http://worldwidewebdotjptdotcom/products/peptidearrays/pepspotsdothtm).

FIGS. 2A-B is a photograph of the results of a screen for α-syn-binding sequences within β-syn protein. FIG. 2A: Decamer peptides corresponding to consecutive overlapping sequences of β-syn were synthesized on a cellulose membrane and incubated with β-syn. The sequence of each spot and its position within the α-syn sequence is mentioned beneath the spot. In the first fifteen amino acids there is one amino acid shift within the decamer peptides. The rest have a five amino acids shift. FIG. 2B. An additional screen was performed using stringent conditions and one amino acid shift along the entire protein. Amino acid sequences of the peptides are provided herein below.

| | |
|---|---|
| MDVFMKGLSM | SEQ ID NO: 23 |
| DVFMKGLSMA | SEQ ID NO: 24 |
| VFMKGLSMAK | SEQ ID NO: 25 |
| FMKGLSMAKE | SEQ ID NO: 26 |
| MKGLSMAKEG | SEQ ID NO: 27 |
| KGLSMAKEGV | SEQ ID NO: 28 |
| GLSMAKEGVV | SEQ ID NO: 29 |
| LSMAKEGVVA | SEQ ID NO: 30 |
| SMAKEGVVAA | SEQ ID NO: 31 |
| MAKEGVVAAA | SEQ ID NO: 32 |
| AKEGVVAAAE | SEQ ID NO: 33 |
| KEGVVAAAEK | SEQ ID NO: 34 |
| EGVVAAAEKT | SEQ ID NO: 35 |
| GVVAAAEKTK | SEQ ID NO: 8 |
| VVAAAEKTKQ | SEQ ID NO: 9 |
| VAAAEKTKQG | SEQ ID NO: 10 |
| KTKQGVTEAA | SEQ ID NO: 36 |
| VTEAAEKTKE | SEQ ID NO: 37 |
| EKTKEGVLYV | SEQ ID NO: 38 |
| GVLYVGSKTR | SEQ ID NO: 1 |
| GSKTREGVVQ | SEQ ID NO: 40 |
| EGVVQGVASV | SEQ ID NO: 41 |
| GVASVAEKTK | SEQ ID NO: 7 |
| LGGAVFSGAG | SEQ ID NO: 11 |
| FSGAGNIAAA | SEQ ID NO: 42 |
| NIAAATGLVK | SEQ ID NO: 43 |
| TGLVKREEFP | SEQ ID N: 44 |
| REEFPTDLKP | SEQ ID NO: 45 |
| TDLKPEEVAQ | SEQ ID NO: 46 |
| EEVAQEAAEE | SEQ ID NO: 47 |
| EAAEEPLIEP | SEQ ID NO: 48 |
| PLIEPLMEPE | SEQ ID NO: 49 |
| LMEPEGESYE | SEQ ID NO: 50 |
| GESYEDPPQE | SEQ ID NO: 51 |
| DPPQEEYQEY | SEQ ID NO: 52 |
| EYQEYEPEA | SEQ ID NO: 53 |
| VLYVGSKTRE | SEQ ID NO: 2 |
| LYVGSKTREG | SEQ ID NO: 3 |
| YVGSKTREGV | SEQ ID NO: 4 |
| AAATGLVKRE | SEQ ID NO: 5 |
| AATGLVKREE | SEQ ID NO: 6 |

FIGS. 3A-K are photographs and graphs illustrating in vitro inhibition of α-syn fibrillar assemblies. FIG. 3A. β-syn peptides were screened for inhibition on α-syn aggregation (molar ratio 20:1 respectively). FIG. 3B. Kinetic analysis of the aggregation of α-syn in the presence of peptides 36 and 39 (SEQ ID NO: 1 and 4). Control As (♦), peptide β-syn 39 with α-syn (▲), peptide β-syn 36 with α-syn (■). FIG. 3C. Dose dependent inhibition effect of peptide β-syn 36 on α-syn aggregation. FIGS. 3D-K. TEM images of α-syn fibrils with several peptides; α-syn alone, β-syn 6short, 36,37,38,39,77, 78. 6 short, 37 and 38 bar=500 nM. Rest of the peptides bar=1 µM.

FIGS. 4A-B are photographs of results of biochemical analysis of α-syn aggregation with and without inhibitors. FIG. 4A. Aggregation of α-syn over time. Soluble oligomers were formed while shaking at 37° C. Detection was carried using Western blot analysis. FIG. 4B. Inhibition of oligomers assembly using β-syn peptides following 24 hours of incubation. Detection was carried using Western blot analysis.

Figure 5A:
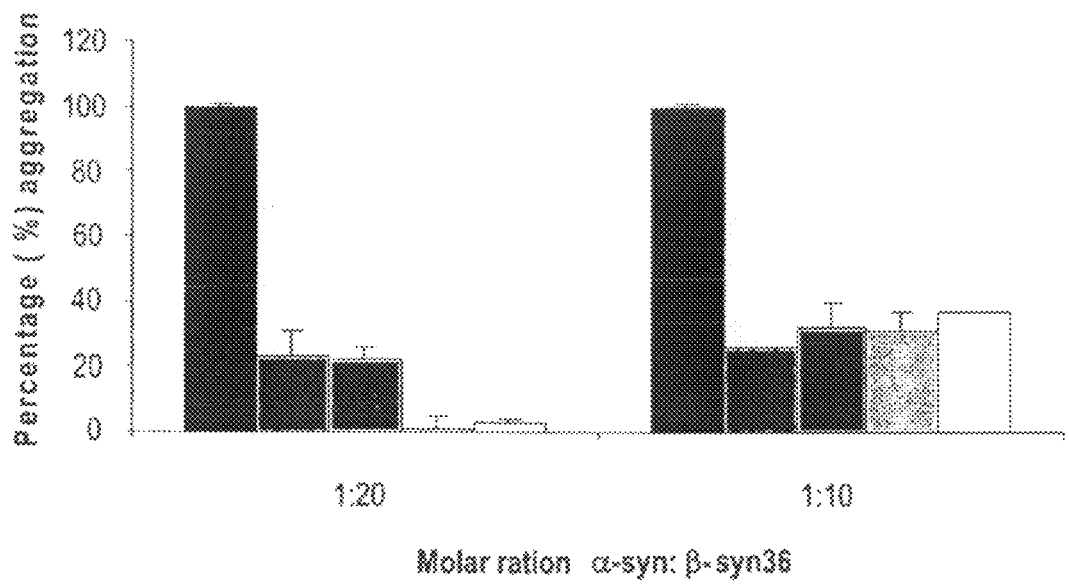
Figure 5B:
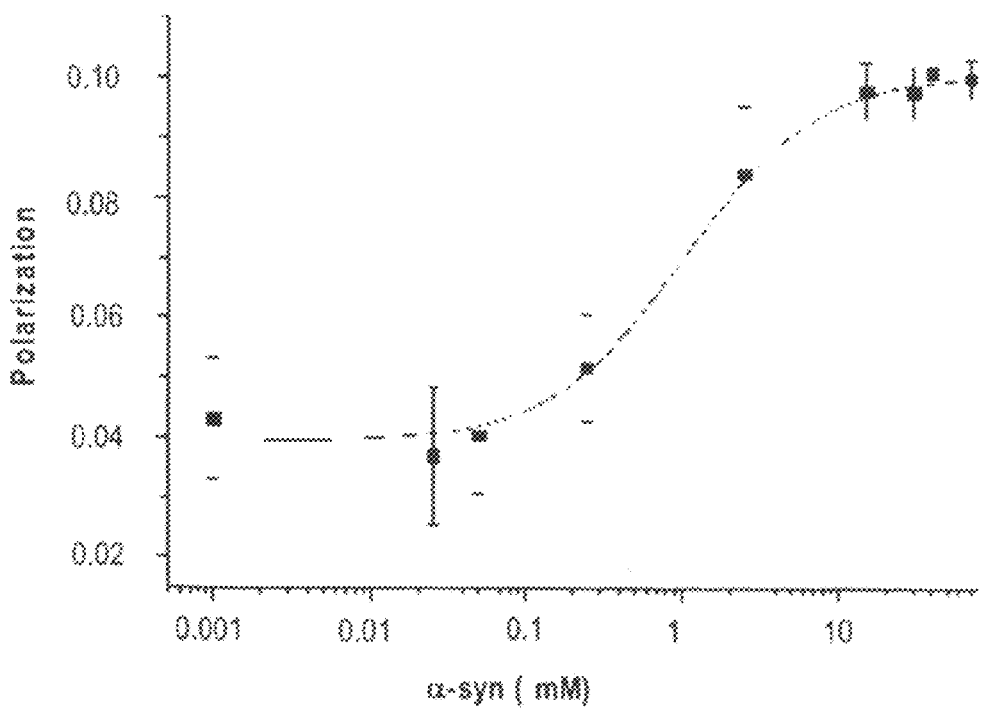

FIGS. 5A-B are graphs illustrating analysis of β-syn modified peptides. FIG. 5A. Inhibition of α-syn fibrilar assemblies using ThT Florescence Assay. Three modified peptides of β-syn 36 were screened for their inhibition on α-syn aggregation. α-syn alone is in black, β-syn 36 with α-syn is in dark grey, and the modified peptides with α-syn are in light grey and white colors, ordered from left to right as β-syn 36D, retro-inverso, retro inverso with amidation and acetylation. The molar ratio of α-syn: peptide were 1:20 and 1:10 respectively. FIG. 5B. The affinity of β-syn 36 containing Tryptophan instead of Tyrosine towards α-syn monomers was examined using fluorescent anisotropy method. Kd=1 µM.

Figure 6A:
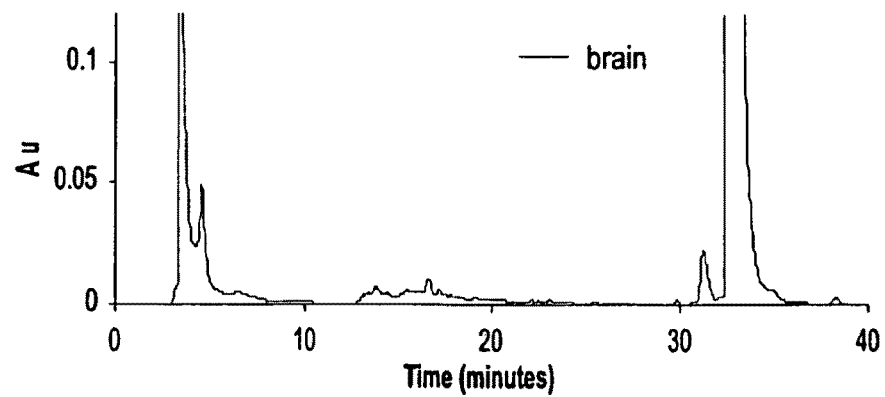
Figure 6B:
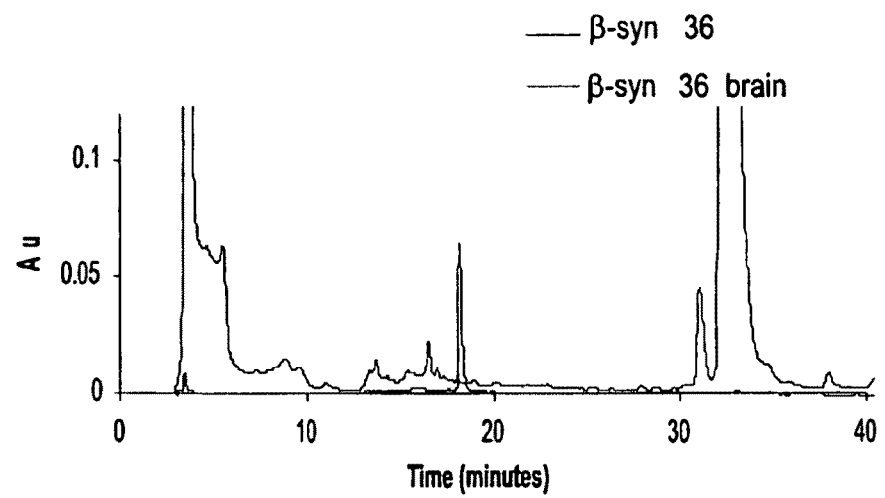
Figure 6C:
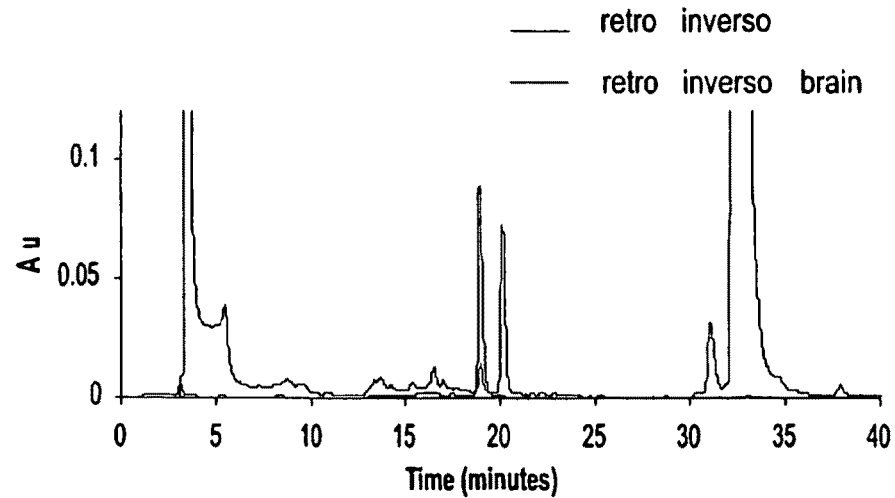

FIGS. 6A-C are HPLC spectra illustrating stability of the peptides in a mouse brain extract. A brain extract of WT ICR white mouse was extracted and incubated with peptides β-syn 36 and β-syn 36 retro inverso for two hours and loaded on C18 column. FIG. 6A Spectra of a mouse brain extract (red). FIG. 6B Spectra of β-syn 36 peptide (blue) and β-syn 36 peptide with brain extract (red). FIG. 6C Spectra of β-syn 36 retro inverso peptide (blue) and β-syn 36 retro inverso peptide with brain extract (red).

Figure 7A:
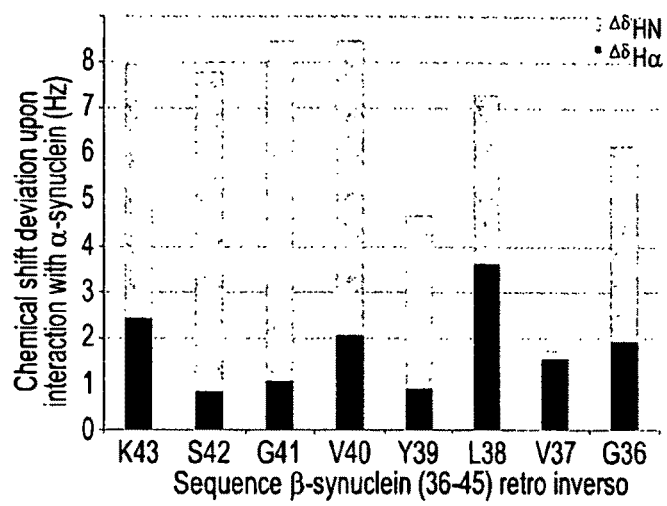
Figure 7B:
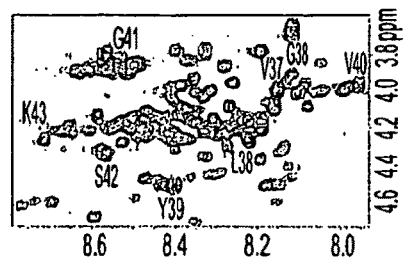
Figure 7C:
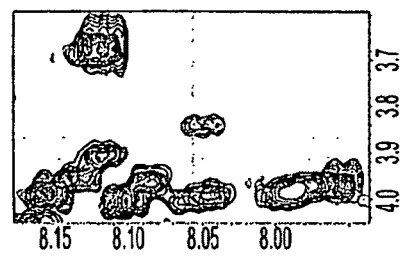
Figure 7D:
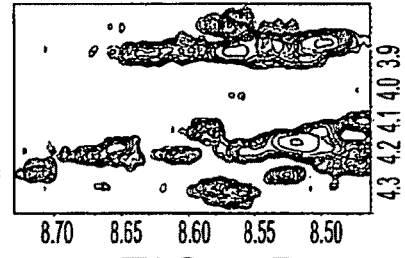
Figure 7F:
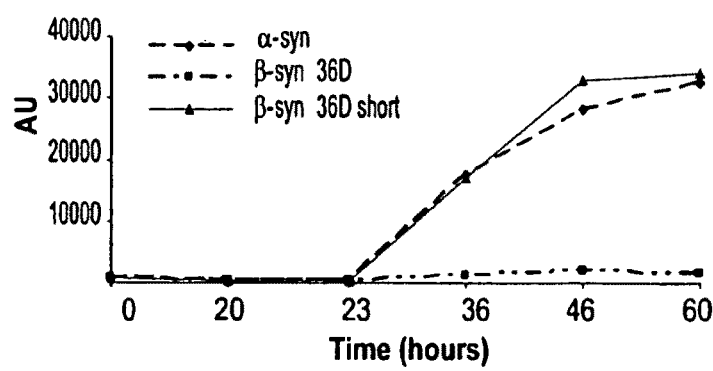
Figure 7E:
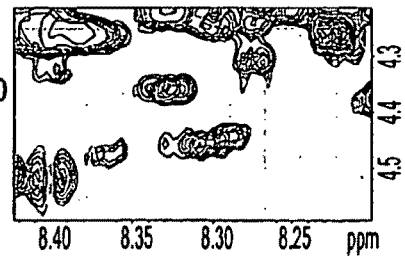

FIGS. 7A-F are graphs and spectra following NMR analysis. Chemical shift deviations of Ha (grey) and HN (black) backbone atoms of retro-inverso peptide upon binding α-syn (FIG. 7A); Ha-HN region of TOCSY spectra overlay of β-syn-derived retro-inverso peptide (red) and α-syn (blue) upon binding (green) (FIG. 7B) and expansions of all the retro-inverso peaks that showed deviations upon binding (FIGS. 7C-E). ThT analysis of α-syn with and without α-syn 36D and β-syn 36D short which lacks amino acids G,V,L (FIG. 7F).

FIGS. 8A-E are photographs illustrating internalization of β-syn 36 retro inverso into the cells. Differentiated SHSY5Y over expressing WT α-syn cells were incubated with 50 µM and 250 µM of FITC conjugated β-syn 36 retro inverso peptide for periods of 0.5 hours, 2 hours and 4 hours. After fixation, the presence of the FITC-conjugated peptide (green) was detected inside the cells. Cellular α-syn was detected using cy5-conjugated antibody (purple) and the membrane was marked with Phalloidin (red). (FIG. 8A) After 30 minutes at 37° C. there was no peptide staining (green). (FIGS. 8B-C) After 2 hours of incubation, no or little amount of peptide was detected inside the cells (green). (FIGS. 8D-E). After 4 hours of incubation, the peptide was clearly detected inside the cells. The peptide's internalization was visualized using an LSM-510 Zeiss confocal microscope.

Figure 9:
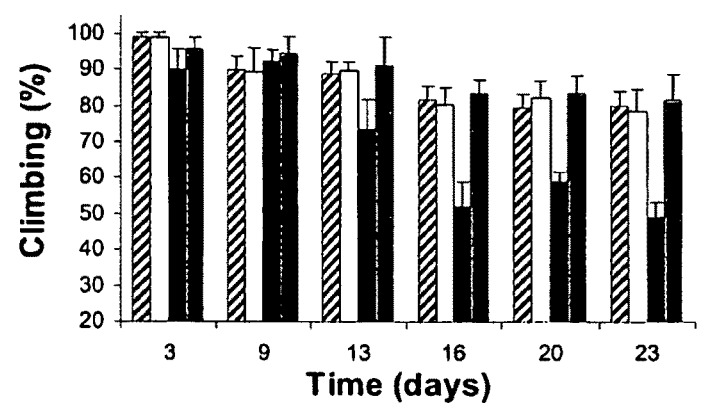

FIG. 9 is a bar graph illustrating results following analysis of locomotive climbing behavior in flies. Four classes of flies, each containing five tubes of ten flies were analyzed using the climbing assay. In black, female offsprings expressing α-syn A53T grown on a regular medium. In grey, female offsprings expressing α-syn A53T grown on medium containing β-syn retro inverso peptide. In striped line, control female offsprings grown on a regular medium. In white, control female offsprings grown on medium containing β-syn retro inverso peptide. Results show the percent of flies which climbed along the test tube after 20 seconds.

Figure 10:
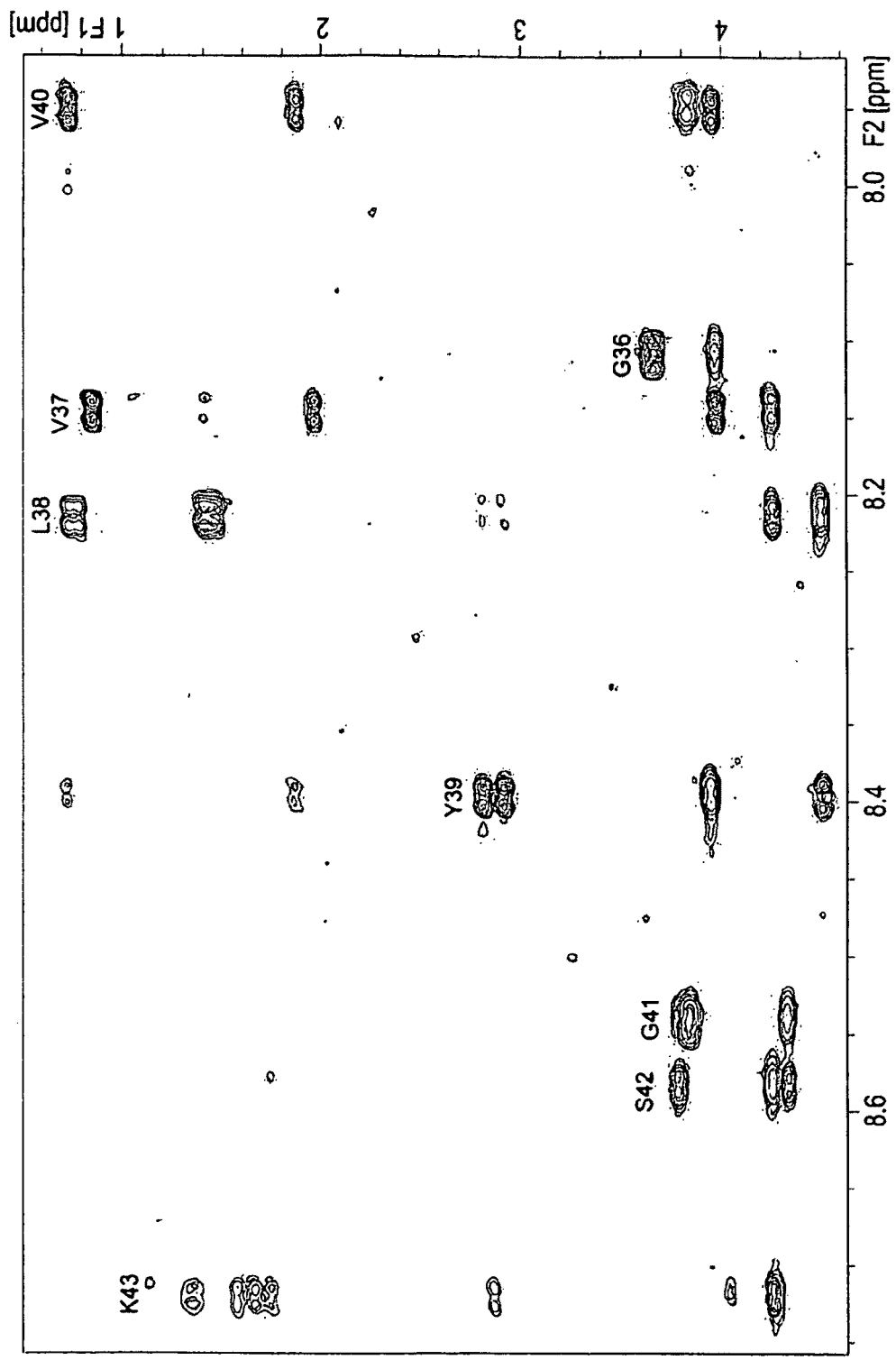

FIG. 10 is an NMR assignment spectra of b-syn 36 retro-inverso peptide: Overlay of HN-Ha interaction regions of TOCSY (red) and NOESY (green) spectra of taken under identical conditions according to which assignment was performed.

DESCRIPTION OF EMBODIMENTS OF THE INVENTION

The present invention, in some embodiments thereof, relates to compositions and methods for treating and preventing neurodegenerative diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The intracellular oligomerization of α-synuclein is associated with Parkinson's disease and other neurodegenerative diseases and is therefore considered an important target for disease-modifying treatment of the disease.

Since beta-synuclein has been shown to inhibit the aggregation of alpha-synuclein in a dose-dependent manner, the present inventors systematically mapped the entire sequence of beta-syn to identify all the domains that have the potential to mediate the molecular recognition events of beta-syn and alpha-syn. A common peptide array technique was used and several interaction regions were found (FIG. 2A). A second membrane was used to confirm these results with stringent experiment conditions (FIG. 2B), which pinpointed the spots that appeared in both membranes. Decamer peptides corresponding to the interaction areas were synthesized and their ability to inhibiting the aggregation of alpha-syn was tested using ThT and TEM assays. Both methods showed correlating results, indicating an inhibitory effect on fibril formation by the peptides (FIGS. 3A-K).

The present inventors further showed that whilst some peptides were capable of inhibiting only one form of the aggregates, other peptides were capable of inhibiting both the soluble and insoluble aggregates of the protein (FIG. 4).

In order to develop the molecular recognition module into a drug-candidate, a retro-inverso analogue of the best peptide inhibitor was designed. While this peptide shows indistinguishable activity as compared to the native peptide, it was shown to be stable in human serum (FIGS. 6A-C) and penetrates α-synuclein over-expressing cells (FIGS. 8AE). NMR analysis mapped the interface of interaction between the D-amino acid peptide and α-synuclein (FIGS. 7A-F). Finally, the administration of the peptide to Drosophila model expressing mutant A53T α-synuclein resulted in a significant recovery of the climbing phenotype in the treated flies (FIG. 9). The present inventors propose that engineered peptides generated according to the teachings of the present invention can serve as a lead for the development of new class of therapeutic agents to treat neurodegenerative diseases, in general, and Parkinson's disease, in particular.

Embodiments of the present invention provide for an isolated peptide being less than 20 amino acids in length, the peptide comprising an amino acid sequence GVASVAEKTK (SEQ ID NO: 7), GVLYVGSKTREGV (SEQ ID NO: 12) AAATGLVKREE (SEQ ID NO: 13) or GVVAAAEKTKQG (SEQ ID NO: 14) of beta synuclein, mimetics and/or a fragment thereof, the peptide being capable of inhibiting alpha-synuclein aggregation.

As used herein "Beta-synuclein" refers to the protein product of SNCB gene, GenBank Accession Number NP_001001502.1 (SEQ ID NO: 15) NP_003076.1 (SEQ ID NO: 16).

The phrase "capable of inhibiting alpha-synuclein aggregation" refers to an ability of reducing alpha-synuclein aggregation (e.g. oligomerization and/or fibril formation) by at least 10%, more preferably by at least 20%, more preferably by at least 30%, more preferably by at least 40%, more preferably by at least 50%, more preferably by at least 60%, more preferably by at least 70%, more preferably by at least 80%, more preferably by at least 90%, more preferably by at least 100%. According to one embodiment the peptide of this aspect of the present invention is capable of inhibiting alpha-synuclein aggregation.

As used herein, the term "fibril" refers to a thread-like filamentous structure composed of higher ordered aggregates which is typically visible in an electron microscope.

Methods of monitoring the ability of the peptides of the present invention to down-regulate alpha-synuclein aggregation are described in Example 3 (by Transmission electron microscopy (TEM) analysis), Example 4 (by Western blot analysis) and Example 6 (Tht binding assays). Other methods are provided in U.S. Pat. No. 6,184,351 and U.S. Patent Application Numbers 2002151464 and 20030027210, each of which is incorporated by reference in its entirety.

The term "isolated" refers to being isolated from a physiological environment or substantially free of other biological material.

The term "peptide" as used herein encompasses native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder. Other modifications (e.g, end-capping) are further described hereinbelow.

The peptide can be 2-20, 2-15, 4-15, 5-15, 4-10 and 5-10 amino acid residues in length. Thus the peptide may consist of, 2, 3, 4, 5, 6, 7, 8, 9, 10, 11, 12, 13, 14, 15, 16, 17, 18, 19 or 20 amino acid residues.

Accordingly, the peptides may comprise or consist of the following exemplary peptides:

| | | |
|---|---|---|
| 36-46. | GVLYVGSKTR | (SEQ ID NO: 1) |
| 37-47. | VLYVGSKTRE | (SEQ ID NO: 2) |
| 38-48. | LYVGSKTREG | (SEQ ID NO: 3) |
| 39-49. | YVGSKTREGV | (SEQ ID NO: 4) |
| 77-87. | AAATGLVKRE | (SEQ ID NO: 5) |
| 78-88. | AATGLVKREE | (SEQ ID NO: 6) |
| 51-61. | GVASVAEKTK | (SEQ ID NO: 7) |
| 14-24. | GVVAAAEKTK | (SEQ ID NO: 8) |
| 15-25. | VVAAAEKTKQ | (SEQ ID NO: 9) |
| 16-26. | VAAAEKTKQG | (SEQ ID NO: 10) |

According to exemplary embodiment the peptide is not YVGSKTREGVV (SEQ ID NO: 17); VAAAEKTKQGV (SEQ ID NO: 18), LS (SEQ ID NO: 19), GL (SEQ ID NO: 20) and KEG (SEQ ID NO: 21), although at least some of these peptides can be used in therapeutic applications according to the present teachings.

According to additional embodiments, the peptide comprises or consists of the amino acid sequence KTR (SEQ ID NO: 58).

According to additional embodiments, the peptide comprises or consists of the amino acid sequence KTRE (SEQ ID NO: 59).

According to additional embodiments, the peptide comprises or consists of the amino acid sequence KTRG (SEQ ID NO: 60).

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

The aromatic amino acid can be any naturally occurring or synthetic aromatic residue including, but not limited to, phenylalanine, tyrosine, tryptophan, phenylglycine, or modificants, precursors or functional aromatic portions thereof. Examples of aromatic residues which can form a part of the peptides of present invention are provided in Table 2 below.

Thus, natural aromatic amino acids, Trp, Tyr and Phe, may be substituted for synthetic non-natural acid such as Phenylglycine, Tic, naphtylalanine (Nal), phenylisoserine, threoninol, ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptide may also comprise conserved amino acid substitutions which may include naturally occurring conserved substitutions or synthetic substitutions see for example Karlin, S., and Ghandour, G., (1985). Multiple alphabet amino acid sequence comparison of the immunoglobulin κchain constant domain. Proceedings of the National Academy of Sciences of the United States of America. 82, 8597-8601.

Amino acid classes:

chemical: acidic (DE), aliphatic (AGILV), amide (NQ), aromatic (FWY), basic (RHK), hydroxyl (ST), imino (P), sulfur (CM);

functional: acidic, basic, hydrophobic (A,I,L,M,F,P,W,V), polar (N,C,Q,G,S,T,Y);

charge: acidic, basic, neutral;

structural: ambivalent (A,C,G,P,S,T,W,Y), external (R,N,D,Q,E,H,K), internal (I,L,M,F,V)

The Single Amino Acid Code is Provided Below.

Tables 1 and 2 below list naturally occurring amino acids (Table 1) and non-conventional or modified amino acids (e.g., synthetic, Table 2) which can be used with the present invention.

TABLE 1

| One-letter Symbol | Three-Letter Abbreviation | Amino Acid |
|---|---|---|
| A | Ala | alanine |
| R | Arg | Arginine |
| N | Asn | Asparagine |
| D | Asp | Aspartic acid |
| C | Cys | Cysteine |
| Q | Gln | Glutamine |
| E | Glu | Glutamic Acid |
| G | Gly | glycine |
| H | His | Histidine |
| I | Iie | isoleucine |
| L | Leu | leucine |
| K | Lys | Lysine |
| M | Met | Methionine |
| F | Phe | phenylalanine |
| P | Pro | Proline |
| S | Ser | Serine |
| T | Thr | Threonine |
| W | Trp | tryptophan |
| Y | Tyr | tyrosine |
| V | Val | Valine |
| X | Xaa | Any amino acid as above |

TABLE 2

| Code | Non-conventional amino acid | Code | Non-conventional amino acid |
|---|---|---|---|
| Nmala | L-N-methylalanine | Abu | α-aminobutyric acid |
| Nmarg | L-N-methylarginine | Mgabu | α-amino-α-methylbutyrate |
| Nmasn | L-N-methylasparagine | Cpro | aminocyclopropane- |
| Nmasp | L-N-methylaspartic acid | | carboxylate |

TABLE 2-continued

| Code | Non-conventional amino acid | Code | Non-conventional amino acid |
|---|---|---|---|
| Nmcys | L-N-methylcysteine | Aib | aminoisobutyric acid |
| Nmgln | L-N-methylglutamine | Norb | aminonorbornyl-carboxylate |
| Nmglu | L-N-methylglutamic acid | | |
| Nmhis | L-N-methylhistidine | Chexa | cyclohexylalanine |
| Nmile | L-N-methylisolleucine | Cpen | cyclopentylalanine |
| Nmleu | L-N-methylleucine | Dal | D-alanine |
| Nmlys | L-N-methyllysine | Darg | D-arginine |
| Nmmet | L-N-methylmethionine | Dasp | D-aspartic acid |
| Nmnle | L-N-methylnorleucine | Dcys | D-cysteine |
| Nmnva | L-N-methylnorvaline | Dgln | D-glutamine |
| Nmorn | L-N-methylornithine | Dglu | D-glutamic acid |
| Nmphe | L-N-methylphenylalanine | Dhis | D-histidine |
| Nmpro | L-N-methylproline | Dile | D-isoleucine |
| Nmser | L-N-methylserine | Dleu | D-leucine |
| Nmthr | L-N-methylthreonine | Dlys | D-lysine |
| Nmtrp | L-N-methyltryptophan | Dmet | D-methionine |
| Nmtyr | L-N-methyltyrosine | Dorn | D-ornithine |
| Nmval | L-N-methylvaline | Dphe | D-phenylalanine |
| Nmetg | L-N-methylethylglycine | Dpro | D-proline |
| Nmtbug | L-N-methyl-t-butylglycine | Dser | D-serine |
| Nle | L-norleucine | Dthr | D-threonine |
| Nva | L-norvaline | Dtrp | D-tryptophan |
| Maib | α-methyl-aminoisobutyrate | Dtyr | D-tyrosine |
| Mgabu | α-methyl-γ-aminobutyrate | Dval | D-valine |
| Mchexa | α-methylcyclohexylalanine | Dmala | D-α-methylalanine |
| Mcpen | α-methylcyclopentylalanine | Dmarg | D-α-methylarginine |
| Manap | α-methyl-α-napthylalanine | Dmasn | D-α-methylasparagine |
| Mpen | α-methylpenicillamine | Dmasp | D-α-methylaspartate |
| Nglu | N-(4-aminobutyl)glycine | Dmcys | D-α-methylcysteine |
| Naeg | N-(2-aminoethyl)glycine | Dmgln | D-α-methylglutamine |
| Norn | N-(3-aminopropyl)glycine | Dmhis | D-α-methylhistidine |
| Nmaabu | N-amino-α-methylbutyrate | Dmile | D-α-methylisoleucine |
| Anap | α-napthylalanine | Dmleu | D-α-methylleucine |
| Nphe | N-benzylglycine | Dmlys | D-α-methyllysine |
| Ngln | N-(2-carbamylethyl)glycine | Dmmet | D-α-methylmethionine |
| Nasn | N-(carbamylmethyl)glycine | Dmorn | D-α-methylornithine |
| Nglu | N-(2-carboxyethyl)glycine | Dmphe | D-α-methylphenylalanine |
| Nasp | N-(carboxymethyl)glycine | Dmpro | D-α-methylproline |
| Ncbut | N-cyclobutylglycine | Dmser | D-α-methylserine |
| Nchep | N-cycloheptylglycine | Dmthr | D-α-methylthreonine |
| Nchex | N-cyclohexylglycine | Dmtrp | D-α-methyltryptophan |
| Ncdec | N-cyclodecylglycine | Dmty | D-α-methyltyrosine |
| Ncdod | N-cyclododeclglycine | Dmval | D-α-methylvaline |
| Ncoct | N-cyclooctylglycine | Dnmala | D-α-methylalnine |
| Ncpro | N-cyclopropylglycine | Dnmarg | D-α-methylarginine |
| Ncund | N-cycloundecylglycine | Dnmasn | D-α-methylasparagine |
| Nbhm | N-(2,2-diphenylethyl)glycine | Dnmasp | D-α-methylasparatate |
| Nbhe | N-(3,3-diphenylpropyl)glycine | Dnmcys | D-α-methylcysteine |
| Nhtrp | N-(3-indolylyethyl) glycine | Dnmleu | D-N-methylleucine |
| Nmgabu | N-methyl-γ-aminobutyrate | Dnmlys | D-N-methyllysine |
| Dnmmet | D-N-methylmethionine | Nmchexa | N-methylcyclohexylalanine |
| Nmcpen | N-methylcyclopentylalanine | Dnmorn | D-N-methylornithine |
| Dnmphe | D-N-methylphenylalanine | Nala | N-methylglycine |
| Dnmpro | D-N-methylproline | Nmaib | N-methylaminoisobutyrate |
| Dnmser | D-N-methylserine | Nile | N-(1-methylpropyl)glycine |
| Dnmser | D-N-methylserine | Nile | N-(2-methylpropyl)glycine |
| Dnmthr | D-N-methylthreonine | Nleu | N-(2-methylpropyl)glycine |
| Nva | N-(1-methylethyl)glycine | Dnmtrp | D-N-methyltryptophan |
| Nmanap | N-methyla-napthylalanine | Dnmtyr | D-N-methyltyrosine |
| Nmpen | N-methylpenicillamine | Dnmval | D-N-methylvaline |
| Nhtyr | N-(p-hydroxyphenyl)glycine | Gabu | γ-aminobutyric acid |
| Ncys | N-(thiomethyl)glycine | Tbug | L-t-butylglycine |
| Pen | penicillamine | Etg | L-ethylglycine |
| Mala | L-α-methylalanine | Hphe | L-homophenylalanine |
| Masn | L-α-methylasparagine | Marg | L-α-methylarginine |
| Mtbug | L-α-methyl-t-butylglycine | Masp | L-α-methylaspartate |
| Metg | L-methylethylglycine | Mcys | L-α-methylcysteine |
| Mglu | L-α-methylglutamate | Mgln | L-α-methylglutamine |
| Mhphe | L-α-methylhomo phenylalanine | Mhis | L-α-methylhistidine |
| Nmet | N-(2-methylthioethyl)glycine | Mile | L-α-methylisoleucine |
| Narg | N-(3-guanidinopropyl)glycine | Dnmgln | D-N-methylglutamine |
| Nthr | N-(1-hydroxyethyl)glycine | Dnmglu | D-N-methylglutamate |
| Nser | N-(hydroxyethyl)glycine | Dnmhis | D-N-methylhistidine |
| Nhis | N-(imidazolylethyl)glycine | Dnmile | D-N-methylisoleucine |
| Nhtrp | N-(3-indolylethyl)glycine | Dnmleu | D-N-methylleucine |
| Nmgabu | N-methyl-γ-aminobutyrate | Dnmlys | D-N-methyllysine |
| Dnmmet | D-N-methylmethionine | Nmchexa | N-methylcyclohexylalanine |
| Nmcpen | N-methylcyclopentylalanine | Dnmorn | D-N-methylornithine |

TABLE 2-continued

| Code | Non-conventional amino acid | Code | Non-conventional amino acid |
| --- | --- | --- | --- |
| Dnmphe | D-N-methylphenylalanine | Nala | N-methylglycine |
| Dnmpro | D-N-methylproline | Nmaib | N-methylaminoisobutyrate |
| Dnmser | D-N-methylserine | Nile | N-(1-methylpropyl)glycine |
| Dnmthr | D-N-methylthreonine | Nleu | N-(2-methylpropyl)glycine |
| Nval | N-(1-methylethyl)glycine | Dnmtrp | D-N-methyltryptophan |
| Nmanap | N-methyla-napthylalanine | Dnmtyr | D-N-methyltyrosine |
| Nmpen | N-methylpenicillamine | Dnmval | D-N-methylvaline |
| Nhtyr | N-(p-hydroxyphenyl)glycine | Gabu | γ-aminobutyric acid |
| Ncys | N-(thiomethyl)glycine | Tbug | L-t-butylglycine |
| Pen | penicillamine | Etg | L-ethylglycine |
| Mala | L-α-methylalanine | Hphe | L-homophenylalanine |
| Masn | L-α-methylasparagine | Marg | L-α-methylarginine |
| Mtbug | L-α-methyl-t-butylglycine | Masp | L-α-methylaspartate |
| Metg | L-methylethylglycine | Mcys | L-α-methylcysteine |
| Mglu | L-α-methylglutamate | Mgln | L-α-methylglutamine |
| Mhphe | L-α-methylhomophenylalanine | Mhis | L-α-methylhistidine |
| Nmet | N-(2-methylthioethyl)glycine | Mile | L-α-methylisoleucine |
| Mlys | L-α-methyllysine | Mleu | L-α-methylleucine |
| Mnle | L-α-methylnorleucine | Mmet | L-α-methylmethionine |
| Morn | L-α-methylornithine | Mnva | L-α-methylnorvaline |
| Mpro | L-α-methylproline | Mphe | L-α-methylphenylalanine |
| Mthr | L-α-methylthreonine | mser | L-α-methylserine |
| Mtyr | L-α-methyltyrosine | Mtrp | L-α-methylvaline |
| Nmhphe | L-N-methylhomophenylalanine | Mval Nnbhm | L-α-methylleucine N-(N-(2,2-diphenylethyl) |
| Nnbhe | N-(N-(3,3-diphenylpropyl) carbamylmethyl(1)glycine | Nnbhm | carbamylmethyl-glycine |
|  |  | Nmbc | 1-carboxy-1-(2,2-diphenyl ethylamino)cyclopropane |

Since the present peptides are preferably utilized in therapeutics or diagnostics which require the peptides to be in soluble form, the peptides of the present invention may include one or more non-natural or natural polar amino acids, including but not limited to serine and threonine which are capable of increasing peptide solubility due to their hydroxyl-containing side chain.

The peptide of some embodiments of the present invention comprises at least 1, 2, 3, 4 or more basic amino acid residues to increase binding to the alpha-synuclein. According to exemplary embodiments the basic amino acid is positioned at an end of the peptide (C and/or N).

Peptides according to some embodiments of the present invention include at least one β-sheet breaker amino acid residue, which is positioned in the peptide sequence as described below. Peptides which include such β-sheet breaker amino acids retain recognition of alpha-synuclein polypeptides but prevent aggregation thereof. According to one embodiment of the present invention, the β-sheet breaker amino acid is a naturally occurring amino acid such as proline, which is characterized by a limited phi angle of about −60 to +25 rather than the typical beta sheet phi angle of about −120 to −140 degrees, thereby disrupting the beta sheet structure of the alpha-synuclein fibril. Other β-sheet breaker amino acid residues include, but are not limited to aspartic acid, glutamic acid, glycine, lysine and serine (according to Chou and Fasman (1978) Annu. Rev. Biochem. 47, 258).

According to another embodiment of this aspect of the present invention, the β-sheet breaker amino acid residue is a synthetic amino acid such as a Cα-methylated amino acid, which conformational constrains are restricted [Balaram, (1999) J. Pept. Res. 54, 195-199]. Unlike natural amino acids, Cα-methylated amino acids have a hydrogen atom attached to the $C_\alpha$, which affects widely their sterical properties regarding the φ and ψ angels of the amide bond and mediate their therapeutic effect more efficiently.

The β-sheet breaker amino acid or aromatic amino acid can be located anywhere in the peptide (N-terminal, C-terminal, or a region flanked by the N or C termini).

According to exemplary embodiments of the present invention, the peptide has an end-cap modification.

The phrase "end-capping modified peptide", as used herein, refers to a peptide which has been modified at the N-(amine) terminus and/or at the C-(carboxyl)terminus thereof. The end-capping modification refers to the attachment of a chemical moiety to the terminus, so as to form a cap. Such a chemical moiety is referred to herein as an end-capping moiety and is typically also referred to herein and in the art, interchangeably, as a peptide protecting moiety or group.

The phrase "end-capping moiety", as used herein, refers to a moiety that when attached to the terminus of the peptide, modifies the end-capping. The end-capping modification typically results in masking the charge of the peptide terminus, and/or altering chemical features thereof, such as, hydrophobicity, hydrophilicity, reactivity, solubility and the like. Examples of moieties suitable for peptide end-capping modification can be found, for example, in Green et al., "Protective Groups in Organic Chemistry", (Wiley, 2.sup.nd ed. 1991) and Harrison et al., "Compendium of Synthetic Organic Methods", Vols. 1-8 (John Wiley and Sons, 1971-1996).

Representative examples of N-terminus end-capping moieties include, but are not limited to, formyl, acetyl (also denoted herein as "Ac"), trifluoroacetyl, benzyl, benzyloxycarbonyl (also denoted herein as "Cbz"), tert-butoxycarbonyl (also denoted herein as "Boc"), trimethylsilyl (also denoted "TMS"), 2-trimethylsilyl-ethanesulfonyl (also denoted "SES"), trityl and substituted trityl groups, allyloxycarbonyl, 9-fluorenylmethyloxycarbonyl (also denoted herein as "Fmoc"), and nitro-veratryloxycarbonyl ("NVOC").

Representative examples of C-terminus end-capping moieties are typically moieties that lead to acylation of the carboxy group at the C-terminus and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group of the C-terminus end-capping may be modified to an amide group.

Other end-capping modifications of peptides include replacement of the amine and/or carboxyl with a different moiety, such as hydroxyl, thiol, halide, alkyl, aryl, alkoxy, aryloxy and the like, as these terms are defined herein.

End-capping moieties can be further classified by their aromaticity. Thus, end-capping moieties can be aromatic or non-aromatic.

Representative examples of non-aromatic end capping moieties suitable for N-terminus modification include, without limitation, formyl, acetyl trifluoroacetyl, tert-butoxycarbonyl, trimethylsilyl, and 2-trimethylsilyl-ethanesulfonyl. Representative examples of non-aromatic end capping moieties suitable for C-terminus modification include, without limitation, amides, allyloxycarbonyl, trialkylsilyl ethers and allyl ethers.

Representative examples of aromatic end capping moieties suitable for N-terminus modification include, without limitation, fluorenylmethyloxycarbonyl (Fmoc). Representative examples of aromatic end capping moieties suitable for C-terminus modification include, without limitation, benzyl, benzyloxycarbonyl (Cbz), trityl and substituted trityl groups.

It will be appreciated that since one of the main obstacles in using short peptides in therapy is their proteolytic degradation by stereospecific cellular proteases, the peptides of the present invention can be synthesized from D-isomers of natural amino acids [i.e., inverso peptide analogues, Tjernberg (1997) J. Biol. Chem. 272:12601-5, Gazit (2002) Curr. Med. Chem. 9:1667-1675].

Additionally, the peptides of the present invention include retro, inverso and retro-inverso analogues thereof. It will be appreciated that complete or extended partial retro-inverso analogues of hormones have generally been found to retain or enhance biological activity. Retro-inversion has also found application in the area of rational design of enzyme inhibitors (see U.S. Pat. No. 6,261,569).

As used herein a "retro peptide" refers to peptides which are made up of L-amino acid residues which are assembled in opposite direction to the native peptide sequence.

Retro-inverso modification of naturally occurring polypeptides involves the synthetic assembly of amino acids with α-carbon stereochemistry opposite to that of the corresponding L-amino acids, i.e., D- or D-allo-amino acids in inverse order to the native peptide sequence. A retro inverso analogue, thus, has reversed termini and reversed direction of peptide bonds, while essentially maintaining the topology of the side chains as in the native peptide sequence.

It will be further appreciated that addition of organic groups such as a cholyl groups to the N-terminal or C-terminal of the peptides of the present invention can improve potency and bioavailability (e.g., crossing the blood brain barrier) of therapeutic peptides [Findeis (1999) Biochemistry 38:6791-6800].

A recently developed system present for crossing the BBB is termed Receptor Mediated Transport (RMT). This system uses monoclonal peptide-mimetic antibodies (MAb's) to help large molecules to cross the BBB [Pardridge W M. Pharm Res 2007; 24(9): 1733-44]. These MAb's are either conjugated or fused to a peptide of interest and then use endogenous receptors to gain entry across the BBB.

According to one embodiment, the peptides of the present invention are attached to a sustained-release enhancing agent. Exemplary sustained-release enhancing agents include, but are not limited to hyaluronic acid (HA), alginic acid (AA), polyhydroxyethyl methacrylate (Poly-HEMA), polyethylene glycol (PEG), glyme and polyisopropylacrylamide.

Attaching the amino acid sequence component of the peptides of the invention to other non-amino acid agents may be by covalent linking, by non-covalent complexion, for example, by complexion to a hydrophobic polymer, which can be degraded or cleaved producing a compound capable of sustained release; by entrapping the amino acid part of the peptide in liposomes or micelles to produce the final peptide of the invention. The association may be by the entrapment of the amino acid sequence within the other component (liposome, micelle) or the impregnation of the amino acid sequence within a polymer to produce the final peptide of the invention.

The compounds of the invention may be linear or cyclic (cyclization may improve stability). Cyclization may take place by any means known in the art. Where the compound is composed predominantly of amino acids, cyclization may be via N- to C-terminal, N-terminal to side chain and N-terminal to backbone, C-terminal to side chain, C-terminal to backbone, side chain to backbone and side chain to side chain, as well as backbone to backbone cyclization. Cyclization of the peptide may also take place through non-amino acid organic moieties comprised in the peptide.

The peptides of the present invention can be biochemically synthesized such as by using standard solid phase techniques. These methods include exclusive solid phase synthesis, partial solid phase synthesis methods, fragment condensation, classical solution synthesis. Solid phase polypeptide synthesis procedures are well known in the art and further described by John Morrow Stewart and Janis Dillaha Young, Solid Phase Polypeptide Syntheses (2nd Ed., Pierce Chemical Company, 1984).

Synthetic peptides can be purified by preparative high performance liquid chromatography [Creighton T. (1983) Proteins, structures and molecular principles. WH Freeman and Co. N.Y.] and the composition of which can be confirmed via amino acid sequencing.

Recombinant techniques may also be used to generate the peptides of the present invention. To produce a peptide of the present invention using recombinant technology, a polynucleotide encoding the peptide of the present invention is ligated into a nucleic acid expression vector, which comprises the polynucleotide sequence under the transcriptional control of a cis-regulatory sequence (e.g., promoter sequence) suitable for directing constitutive, tissue specific or inducible transcription of the polypeptides of the present invention in the host cells.

In addition to being synthesizable in host cells, the polypeptide of the present invention can also be synthesized using in vitro expression systems. These methods are well known in the art and the components of the system are commercially available.

Peptides of some embodiments of the present invention can be used for treating or preventing alpha-synucleic associated medical conditions (i.e., medical conditions in which aggregation of alpha synuclein is associated with onset or progression). Examples of such medical conditions include but are not limited to neurodegenerative diseases in particular Alzheimer's disease, the Lewy Body variant of Alzheimer's disease, Parkinson's disease, the multisystem atrophy, the Lewy Body dementia and Huntington's chorea.

The peptides can be provided to an individual per se, or as part of a pharmaceutical composition where it is mixed with a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the peptide preparation, which is accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into a specific region of the brain.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethyl-cellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. Following initial estimate determination, a dose can be formulated in animal models and such information can be used to more accurately determine useful doses in humans. The present inventors have shown that flies may be used as an in vivo model for analyzing the effects of the peptides of the present invention—see Example 9 and Crowther et al, Current Opinion in Pharmacology; 2004, 4:513-516, incorporated herein by reference.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

As well as therapeutic applications, peptides of some embodiments of the present invention can be used for detecting the presence or level of alpha synuclein monomers.

This relies on the peptide's ability to bind the monomeric alpha synuclein form. As such, this may be of used for diagnosis or monitoring treatment efficiency, by indirectly determining the level of the deleterious aggregated form of the protein.

It will be appreciated that the peptides may also serve as tools for studying the interactions between α-syn and β-syn, as well as to aid in the understanding of the role and/or mechanism of β-syn.

To this end, the peptide may be attached to an identifiable moiety. The identifiable moiety can be a member of a binding pair, which is identifiable via its interaction with an additional member of the binding pair and a label which is directly visualized. In one example, the member of the binding pair is an antigen which is identified by a corresponding labeled antibody. In one example, the label is a fluorescent protein or an enzyme producing a colorimetric reaction.

Table 3 below provides examples of sequences of identifiable moieties.

TABLE 3

| Nucleic Acid sequence (Genebank Accession No.) | Amino Acid sequence (Genebank Accession No.) | Identifiable Moiety |
|---|---|---|
| AF435427 | AAL33912 | Green Fluorescent protein |
| AY042185 | AAK73766 | Alkaline phosphatase |
| NM_124071 | NP_568674 | Peroxidase |
| AF329457 | AAK09208 | Histidine tag |
| AF329457 | AF329457 | Myc tag |
| NC_003366 | NP_561589 | Biotin lygase tag |
| AF435432 | AAL33917 | orange fluorescent protein |
| NM_125776 | NM_125776 | Beta galactosidase |
| AF098239 | AAF22695 | Fluorescein isothiocyanate |
| S11540 | S11540 | Streptavidin |

It will be appreciated that such fusions can be effected using chemical conjugation or recombinant DNA technology. The level of the monomeric form is compared to a control sample (e.g., from healthy subject, same subject before treatment, and the like). For research purposes and drug development, e.g., effect of agents on alpha synuclein aggregation, the level of the monomeric form is determined following and optionally prior to treatment with the agent, whereby the agent can be a peptide of the present invention.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Peptide array: The molecular mapping of β-syn binding sequences was performed using peptide array technology. Decamer peptides corresponding to the overlapping sequences of full length 134 amino acids β-syn protein were synthesized on a cellulose membrane matrix. The peptides were covalently bound to a Whatman 50 cellulose support by the C-terminal amino acid residues. After blocking, the membrane was incubated in the presence of N-terminal histidine tagged recombinant α-syn, followed by HRP conjugated anti His monoclonal antibody. A negative control was performed. The immunoblots on the cellulose membrane were developed using Western blot analysis. Once β-syn binding sites on α-syn were identified, small β-syn derived peptides were synthesized.

Expression and purification of α-syn: The protein was expressed in pT7-7 BL21 bacteria. For expression, bacteria cultures were grown to logarithmic stage with ampicillin (100 mg/L) and protein expression was induced using IPTG (1 mM) for 3 hours. The bacteria pellet was re-suspended with TEN buffer (50 mM Tris pH 8.0, 10 mM EDTA, 150 mM NaCl), and frozen at −80° C. until purification.

The purification was accomplished using a non-chromatographic method as described by Volles and Lansbury (Volles and Lansbury, 2007, J Mol Biol 366(5), 1510-1522). Briefly, after boiling and centrifugation of the bacteria, the supernatant was removed to a fresh tube and streptomycin sulfate (136 μL of a 10% solution/mL supernatant) and acetic acid (glacial, 228 μL/mL supernatant) were added, followed by an additional spin for 2 minutes. The supernatant was again removed and then precipitated with ammonium sulfate (saturated ammonium sulfate at 4° C. was used 1:1 vol:vol with supernatant). The precipitated protein was collected by centrifugation (at this stage clones not producing purifiable protein are observed to form no precipitate), and the pellet was washed once with 1 mL ammonium sulfate solution (4° C.; 1:1 vol:vol saturated ammonium sulfate (4° C.): water). The washed pellet was re-suspended in 900 μL 100 mM ammonium acetate (to form a cloudy solution) and precipitated by adding an equal volume of ethanol at room temperature. Ethanol precipitation was repeated once more, followed by a final re-suspension in 100 mM ammonium acetate, O.N. dialysis to water at 4° C., freezing in liquid nitrogen, and lyophilization.

For comparison, the protein was later purified with an additional method using chromatographs and was tested for aggregation inhibition using the same peptides. Briefly, the bacteria pellet was re-suspended in 50 mM Tris, 50 mM KCl, 5 mM MgAc, 0.1% NaN, pH 8.5 and supplemented with 300 uM PMSF inhibitors. The solution was then sonicated and ultracentrifuged for 30 minutes at 14000 RPM at 4° C. The supernatant was then boiled for 15 minutes in a water bath. To separate the precipitated proteins from the solution, the sample was centrifuged for 20 minutes at a speed of 7000 RPM at 4° C. The supernatant was filtered through a 0.45 μm filter and kept for further purification.

The filtrated supernatant was subjected on a HiPrep 16/10 QFF anion exchange column. At 20 mM Tris, pH 8, α-syn has a net negative charge, and can therefore interact with the positively charged moieties (NH$^+$) of the anion exchange column. The protein was eluted using 30-40% of 20 mM Tris and 1M NaCl solution (pH 8) and subjected on a HiLoad 26/20 superdex 200 size exclusion column. Anion exchange fractions were loaded with 50 mM Tris/HCl and 150 mM NaCl buffer (pH 7.5), and the monomer fraction was analyzed by SDSPAGE and collected, dialyzed O.N. to water at 4° C., frozen in liquid nitrogen, and lyophilized.

ThT florescence assay: α-syn was dissolved to a concentration of 200 μM in 100 mM Tris buffer (pH 7.4). In order to obtain the monomeric fraction, the protein was filtered through a 100 kDa centricon. Since α-syn is not a globular protein but a natively unfolded one, only monomers and some dimers pass through the filter. The monomeric protein was immediately mixed with or without different β-syn derived peptides at a 1:1 ration to a final concentration of 100 μM. The samples were incubated at 37° C. with agitation of 850 RPM as described by Tsigelny et al. (Tsigelny et al., 2007 Febs J 274(7), 1862-1877) and the fibrillogenesis rate was followed by thioflavin T (ThT) fluorescence assay (excitation at 450 nm, 2.5 nm slit, and emission at 480 nm, 5 nm slit), after three days of incubation. ThT was added to a 500-fold diluted sample and measured using a Jobin Yvon Horiba Fluoromax 3 fluorimeter.

Transmission electron microscopy: Samples (10 μL) from the α-syn ThT fluorescence assay (with and without inhibitors) were placed on 400-mesh copper grids covered by carbon-stabilized Formvar film (SPI Supplies, West Chester, Pa.). After 1.5 minutes, excess fluid was removed, and the grids were negatively stained with 10 μl of 2% uranyl acetate solution for 2 minutes. Finally, excess fluid was removed and the samples were viewed in a JEOL 1200EX electron microscope operating at 80 kV.

Determination of soluble oligomer formation: Monomeric α-syn was dissolved to a concentration of 200 μM in 100 mM Tris buffer (pH 7.4) and was immediately mixed with or without different β-syn derived peptides at a 1:1 ration to a final concentration of 100 μM, as was described above for the aggregation assay. After the samples were agitated at 37° C. for several days, 10 μl of the protein were centrifuged at 13000 RPM for 10 minutes, the supernatant was collected and electrophoresed in acrylamide gel using native loading buffer without β-mercaptoethanol and boiling. The gel was washed 3 times in ddH$_2$O and samples were then transferred to the nitrocellulose membrane using semi-dry blot technique applying 323 mA current for 30 minutes. The membrane was blocked for 1 hour using 5% milk diluted in TBS (0.3% Tween) while shaking. Anti α-syn diluted 1:1000 (Santa Cruz Biotechnology) in 5% milk in TBS (0.3% tween) was added to the membrane for 2 hours incubation followed by several washes with TBS (0.3% Tween). Rabbit anti mouse IgG (Fc specific)-HRP conjugated antibody diluted 1:5000 in 5% milk diluted in TBS (0.3% Tween) was administrated for 1 hour at RT while shaking. Blots were developed after thorough TBS (0.3% Tween) washes using Enhanced Chemiluminescence System (ECL) according to the manufacturer's instructions.

Fluorescence anisotropy studies: β-syn 36 in which tyrosine was substituted with tryptophan (SEQ ID NO: 22—GVLWVGSKTR) was dissolved to a concentration of 54 μM. The solution was immediately mixed with α-syn monomer stock solution to varying final concentrations. The peptide polarization measurements were carried out using an ISS K2 fluorometer. The solutions were excited at 280 nm and emission was monitored at 350 nm. For each single point, at least five measurements were collected and their average values were used for the calculation. All experiments were performed using ultra pure water.

NMR analysis: Samples were prepared from peptides in lyophilized form dissolved in a solution containing 10% deuterium oxide in 20 mM phosphate buffer and 50 mM NaCl in DDW. When α-syn was used, the sample was prepared in 20 mM phosphate solution as described above, and NaCl and deuterium oxide were added to achieve the above-mentioned concentrations, and the lyophilized peptide was added at the designated molar ratio. pH was measured for all samples. Samples were prepared in Shigemi tubes with a final volume of 260 μL.

The NMR experiments were performed on a Bruker Avance 600 MHz DMX spectrometer operating at the proton frequency of 600.13 MHz using a 5 mm selective probe equipped with a self-shielded xyz-gradient coil. The transmitter frequency was set on the HDO signal, which was calibrated according to temperature (4° C.—4.974 ppm; 10° C.—4.821 ppm; 15° C.—4.773 ppm; 37° C.—4.658 ppm). TOSCY (44) and NOESY (46) experiments were acquired for each temperature and sample set.

Spectra were processed and analyzed with TOPSPIN software (Bruker Analytische Messtechnik GmbH). Zero filling in the indirect dimension and data apodization with a shifted squared sine bell window functions in both dimensions were applied prior to Fourier transformation for optimal resolution. The baseline was further corrected in the direct dimension with a quadratic polynomial function.

Resonance assignment was done according to the sequential assignment methodology developed by Wüthrich based on the TOCSY and NOESY spectra measured under identical experimental conditions. Chemical shift deviations of the HN-Hα peaks were read from carefully calibrated, highly resolved, strongly apodized overlaid 2D spectra.

In vitro assay of peptide stability: Peptides were dissolved to form a 1 mM solution in 50 μM Tris buffer (PH=7.6). 120 μl of the peptide solution was diluted into a 10% freshly-taken mouse brain homogenate without the cerebellum (in 1× Tris buffer and 0.5% Triton X-100). A mixture containing 20% peptide solution and 80% mouse brain homogenate was incubated at 37° C. with delicate shaking for 2 hours. The enzyme reaction was stopped by the addition of 0.1 M HCL solution, followed by denaturation of the protein using CH$_3$OH and incubation at 20° C. for 1 hour. The precipitated proteins were centrifuged at 29,000×g for 20 minutes at 4° C. and the supernatant containing the peptide was concentrated under vacuum and separated using a C18 HPLC column. The area of the peak (UV absorbance at 280 nm) corresponding to the intact peptide was compared with an equivalent sample incubated in 50 µM Tris buffer.

Cell line: SH-SY5Y cells, stably transfected with wild type α-syn, were maintained with DMEM: F12 1:1 containing 5% fetal bovine serum, 2 mM 1-glutamine, 1000 U/ml penicillin-G sodium, 1 mg/ml streptomycin sulfate and 1 mM sodium pyruvate under selective conditions with 100 µM G-418 at 37° C. with 5% $CO_2$. Cells underwent differentiation with 10 µM retinoic acid (Sigma) in complete growth medium, replaced every two days for a period of eight days.

Peptide internalization into SH-SY5Y cells: Peptide internalization into SH-SY5Y cells was visualized by immunocytochemistry staining. $10^4$ cells were seeded on a cover slip coated with poly-L-lysine (0.1%) in a 24-well plate and underwent differentiation as described. Differentiated cells were incubated with the peptide in the cells growth medium for 30 minutes to four hours at 37° C. Cells were washed with PBS and fixed with 4% paraformaldehyde in PBS for 30 minutes at RT and then washed twice with PBS and permeabilized with 0.1% Triton in PBS for 2 minutes. Following two PBS washes, cells were blocked with 10% normal goat serum in 3% BSA for 30 minutes and incubated with anti α-syn antibody (Santa Cruz Biotechnology) diluted 1:1000 and Phalloidin 4 µg/ml (Sigma) for one hour, followed by an additional hour of incubation with Cy5-conjugated goat anti-rabbit IgG (Jackson ImmunoResearch). After being thoroughly washed with PBS, cells were mounted using ProLong Antifade (Invitrogene). Images were taken with LSM510 confocal microscope (Zeiss).

Fly keeping: Flies were reared on standard corneal-molasses medium and were kept at 25° C. Male flies were crossed with virgin females collected no longer than 8 hours or 18 hours after eclosion at 25° C. or 18° C. respectively. Adult offspring (F1) from the crosses were collected up to 9 days after the beginning of their eclosion at 25° C. in order to avoid offspring from the next generation (F2).

Fly crossing: Male flies carrying the driver elav-Gal4 on their X chromosome were crossed with females carrying the A53T α-syn transgene located on their X chromosome under the UAS promoter. This resulted in first generation (F1) female offspring expressing A53T α-syn in their nervous system which served as a PD Drosophila model. Offspring of male flies carrying the driver elav-Gal4 crossed with WT OR females served as control.

Special fly feeding: β-syn retro-inverso peptide was added to standard corneal-molasses medium at a concentration of 0.75 mg/ml. The peptide was mixed thoroughly into the medium at 40° C. and the mixture was aliquot into rearing vials. The vials were kept at 4° C. until use. Crosses were performed either on regular Drosophila medium (control) or on medium supplemented with the peptide. Animals were fed on the appropriate medium from the beginning of the larval stage. After eclosion, offspring were transferred into a new vial that was pre-dripped with 0.75 mg/ml peptide solution every second day.

Locomotive (climbing) assay: Test tubes, each containing 10 flies, were tapped gently on the table and were let stand for 20 seconds. The percent of flies which climbed about one centimeter from the bottom of the test tube was then calculated over time. Each class had five independent test tube repeats.

Example 1

Identification of the Recognition Site Between α and β-syn

Results

In order to determine the interaction sites between the two proteins, both proteins were systematically mapped using a reciprocal peptide-array analysis (FIGS. 1A-D).

The rational behind this assay was to identify domains that have the potential to facilitate the molecular recognition events that lead to interaction. The domains will be the base for synthesizing small derived peptides that might therapeutically be used for inhibition of α-syn aggregation.

The molecular mapping of α and β-syn binding sequences was performed using peptide array technology. Decamer peptides corresponding to the overlapping sequences of the full length 140 amino acid α-syn and 134 amino acid β-syn proteins were synthesized on a cellulose membrane matrix (see FIGS. 2A-B). The peptides were covalently bound to a Whatman 50 cellulose support by the C-terminal amino acid residues.

After blocking, the α and β-syn cellulose membranes were incubated in the presence of N-terminal histidine tagged recombinant α-syn and recombinant β-syn, respectively, followed by HRP conjugated anti his monoclonal antibody. A negative control was performed. The immunoblots on the cellulose membrane were developed using Western blot analysis. Once β-syn binding sites on α-syn were identified, small β-m syn derived peptides were synthesized.

Several decamer-peptides were selected and synthesized for further analysis. These peptides were termed β-syn 6, 14, 36, 37, 38, 39, 77, and 78 according to the location of their first amino acid on the membrane (Table 4, herein below). A seven amino acids peptide (termed 6short), was used as a positive control selected as a good inhibitor candidate by Windisch et al (Windisch et al., 2004 (2004) J Mol Neurosci 24(1), 155-165)—SMAKEGV (SEQ ID NO: 39).

TABLE 4

| aa position within β-syn protein | aa sequence | Peptide's name |
|---|---|---|
| 9-15 | SMAKEGV (SEQ ID NO: 39) | β-syn 6short (control) |
| 14-23 | GVVAAAEKTK (SEQ ID NO: 8) | β-syn 14 |
| 36-45 | GVLYVGSKTR (SEQ ID NO: 1) | β-syn 36 |
| 37-46 | VLYVGSKTRE (SEQ ID NO: 2) | β-syn 37 |
| 38-47 | LYVGSKTREG (SEQ ID NO: 3) | β-syn 38 |

TABLE 4-continued

| aa position within β-syn protein | aa sequence | Peptide's name |
|---|---|---|
| 39-48 | YVGSKTREGV (SEQ ID NO: 4) | β-syn 39 |
| 77-86 | AAATGLVKRE (SEQ ID NO: 5) | β-syn 77 |
| 78-87 | AATGLVKREE (SEQ ID NO: 6) | β-syn 78 |
| β-syn 36 modifications (all aa are D enantiomers) | | |
| 36-45 | GVLYVGSKTR (SEQ ID NO: 54) | D aa β-syn 36 |
| 36-45 | RTKSGVYLVG (SEQ ID NO: 55) | Retro inverso β-syn 36 |
| 36-45 | Acetyl-RTKSGVYLVG-amide (SEQ ID NO: 56) | Acetylated and amidated retro inverso β-syn 36 |
| 39-45 | YVGSKTR (SEQ ID NO: 57) | D aa β-syn 36 short |

Special attention was paid to peptides 36-39 (SEQ ID NOs 1-4) due to the presence of tyrosine. A key role for aromatic amino acids has been identified in the formation of amyloid fibrils through π-stacking interactions [Azriel, R., and Gazit, E. (2001) *J. Biol. Chem.* (276), 34156-34161; Gazit, E. (2002) *Bioinformatics* (18), 880-883; Porat, Y., Kolusheva, S., Jelinek, R., and Gazit, E. (2003) *Biochemistry* (42), 10971-10977; Mazor, Y., Gilead, S., Benhar, I., and Gazit, E. (2002) *J. Mol. Biol.* (322), 1013-1024; Reches, M., and Gazit, E. (2003) *Science* (300), 625-627; Reches, M., and Gazit, E. (2004) *Amyloid* (11), 81-89]. Therefore, the presence of tyrosine within the inhibitor peptides might promote interfering with the self-assembly of the amyloid structures.

Example 2

Inhibition of Amyloid Fibril Formation by β-syn Derived Peptides

In order to examine the inhibitory effect of the peptides on α-syn fibril formation, the Thioflavin-T (ThT) binding assay was used. This method provides quantitative information on amyloid fibril growth. α-syn was incubated for several days at 37° C. with vigorous shaking to allow the formation of amyloid fibrils with or without the different β-syn-derived peptides. The fibrillization process was monitored for three days. FIG. 3A shows that the formation of amyloid fibrils was significantly reduced in the presence of several peptides inhibitors. A kinetic analysis was performed for the two potential inhibitors β-syn 36 and β-syn 39 as these two peptides represent the first and last peptides screened within the aromatic region (FIG. 3B). β-syn 36 showed better inhibition and dose-dependent inhibition tests revealed that the peptide is still efficient at an excess of 10:1 (molar ratio) but less efficient at an excess of 5:1 (FIG. 3C).

Example 3

TEM Analysis of α-syn Aggregation

Transmission electron microscopy (TEM) analysis was performed on samples of α-syn with and without the β-syn inhibitors. The samples were taken from the ThT experiment (presented in FIG. 3A. While the fibrils formed by α-syn alone were large broad ribbon-like fibrils (FIG. 3D), only short or none fibrils were detected in the presence of β-syn peptides. β-syn 36 almost completely inhibited fibril formation (FIG. 3F). These results are highly correlated with the ThT assay results.

Example 4

Screening for Inhibition of Oligomer Formation

To examine the ability of the peptides to inhibit the early stage of aggregation, soluble fractions of α-syn were collected after incubation with the β-syn peptides. The reaction mixtures were separated using SDS-PAGE followed by western blot analysis using a specific anti α-syn antibody (Santa-Cruz) (FIG. 4A). A preliminary test of oligomer formation over time revealed that high oligomers were detected after ~20 hours of incubation; therefore samples were collected after this period of time. The β-syn 6short peptide (our positive control peptide) and peptide β-syn 37 peptide inhibited the fibrils but not the oligomers formation, while peptide β-syn 78 peptide inhibited oligomers but not fibril formation. The β-syn 36 peptide inhibited almost completely the formation of both aggregation types (FIG. 4B).

Example 5

Characterization of the Affinity Between β-syn 36 Peptide and α-syn

To determine the affinity of the interaction between β-syn 36 and α-syn monomers, a peptide containing tryptophan instead of tyrosine at position 39 within β-syn was used, exploiting its intrinsic fluorescence in a fluorescence anisotropy assay. This peptide was found to inhibit α-syn aggregation in a similar manner as β-syn 36 (data not shown). Increasing amount of α-syn monomers were titrated into a solution of β-syn 36 peptide and anisotropy was determined (FIG. 5B). The affinity constant was calculated as ~1 μM.

Example 6

Modified Peptides of β-syn 36 Inhibit the Aggregation of α-syn and Increase Serum Stability In order to enhance the half-life of a peptide in serum, it may be altered to reduce degradation by tissue and serum proteases and peptidases. β-syn 36 is a decamer peptide comprising natural L-amino acids. Since the peptide is susceptible to proteolytic degradation, the present inventors designed a more stable derivate (see Table 1 herein above). For that purpose, three modified peptides were designed; the first composed of D amino acids instead of L, termed β-syn 36D, the second was analogous with retro-inversion of the amino acids sequence, termed retro-inverso. To negate the terminal negative and positive charges of the retro-inverso peptide, a third modified N-terminal acetylated and C-terminus amidated peptide was synthesized, the retro-inverso peptide with amidation and acetylation. The modifications of these peptides were suspected to alter the efficacy of the lead peptide but be required to restore their biological activity. For that purpose, all three peptides were tested for inhibition of α-syn fibril formation using ThT binding assay with a molar ratio of 1:20, 1:10 in favor of the peptides, and showed a similar biological effect to β-syn 36 (FIG. 5A).

Later, the stability of peptide β-syn 36 and the modified retro-inverso peptide was compared using fresh mouse brain homogenate to model serum degradation for a period of 2 hours. The results presented in FIGS. 6A-C indicate an elevation in stability within the modified peptide.

Example 7

NMR Analysis

The residues that participate in the intermolecular interactions of α-syn were determined by following changes in chemical shift upon binding. Obvious overlap between two identical molecules was overcome by using the β-syn 36 retro-inverso peptide (all D amino acids; $R_{45}T_{44}K_{43}S_{42}G_{41}V_{40}Y_{39}L_{38}V_{37}G_{36}$) in interaction with α-syn. All residues of the peptide were identified and assigned (FIG. 10). $R_{45}$ and $T_{44}$ were not seen in the amide region, but were identified in the aliphatic region. The peptide spectrum alone and in interaction with α-syn was determined under a number of conditions: Molar ratios of 1:1 and 1:5 peptide to protein; peptide concentrations of 160 and 400 μM; temperatures of 4° C., 10° C., 20° C., 25° C., and 37° C.; and using the Y39W β-syn 36 retro-inverso analog. In all samples some of the N-terminal region amide signals were lost between R45 and G41, however all samples showed the general trend found for the sample of β-syn 36 retro-inverso with α-syn at a 1:1 molar ratio, 160 μM, 4° C., at pH (FIGS. 7A and B-E and Table 4, herein above). The chemical shifts showed stronger deviations in residues $K_{43}$, $V_{40}$, $L_{38}$ and $G_{36}$. To further highlight the importance of $L_{38}$ and $G_{36}$, β-syn 36D peptide which lacks the first three amino acids—G, V and L was synthesized and showed no inhibition effect on α-syn aggregation using ThT assay (FIG. 7F).

Example 8

Peptide Internalization to Mammalian Cells

To achieve a cellular model of PD, SH-SY5Y5 cells overexpressing wild type α-syn were first subjected to retinoic acid treatment to induce cell differentiation (Lev et al., (2006) Neurosci Lett 399(1-2), 27-32). After 8 days of treatment, cells were cultured in fresh growing media for 0.5-4 hours followed by incubation with FITC-conjugated β-syn 36 retro-inverso peptide (green fluorescence). After incubation, cells were washed, fixed, and permeabilized. The overexpression of wild type α-syn was detected using cy5-conjugated goat anti rabbit antibody (purple fluorescence) and the cell membrane was marked using Phalloidin reagent (red fluorescence). Fluorescent labeling was visualized using an LSM-510 Zeiss confocal microscope (FIGS. 8A-E). Two different concentrations of the peptide were examined—50 μM and 250 μM, showing similar results. After 30 minutes of incubation the peptide didn't enter the cells. Nevertheless, no attachment to the cells was detected. After 2 hours of incubation the peptide was detected mostly on the cell surface. Little amount was detected inside the cell in the concentration of 250 μM. After 4 hours of incubation, the peptide was clearly noted inside the cells.

Example 9

The Effect of β-syn 36 Retro-inverso Peptide in an in vivo Transgenic Fly System In order to assess the effect of the peptide on α-syn in the living organism, a Drosophila model of PD was used. The transgenic flies over express the mutated A53P α-syn in their nervous system, via the Gal4-UAS system. A common behavioral phenotype of these flies is defective locomotion; while normal flies tend to climb up along the tube, these flies remain at the bottom (Ueda et al., (1993) Proc Natl Acad Sci USA 90(23), 11282-11286). Crossing male flies carrying the pan-neuronal elav-Gal4 driver (on their X chromosome) with females carrying the UAS-regulated A53T α-syn transgene resulted in female offspring expressing A53T α-syn in their nervous system. This cross was performed either on regular Drosophila medium or on medium supplemented with 0.75 mg/mL β-syn 36 retro-inverso peptide. The climbing ability of the flies was monitored for 27 days, showing 37% climbing of the untreated PD flies at day 27 in comparison with 66% of the treated flies, revealing an increase of 30% comparing to untreated group. The peptide had no significant effect on locomotion of the control flies. These results revealed a great phenotypic recovery of the A53T α-syn flies using the β-syn 36 retro-inverso peptide.

REFERENCES

Other References are Cited Throughout the Text

1. Sipe, J. D. (1992) *Annu Rev Biochem* 61, 947-975
2. Wetzel, R. (1994) *Trends Biotechnol* 12(5), 193-198
3. Harrison, R. S., Sharpe, P. C., Singh, Y., and Fairlie, D. P. (2007) *Rev Physiol Biochem Pharmacol* (159), 1-77
4. Sipe, J. D., and Cohen, A. S. (2000) *J. Struct. Biol.* (130), 88-98
5. Rochet, J. C., Conway, K. A., and Lansbury, P. T., Jr. (2000) *Biochemistry* 39(35), 10619-10626
6. Serpell, L. C. (2000) *Biochim. Biophys. Acta* (1502), 16-30
7. Dobson, C. M. (2001) *Philos. Trans. R. Soc. Lond. B. Biol. Sci.* (356), 133-144
8. Gazit, E. (2002) *Faseb J* 16(1), 77-83
9. Sacchettini, J. C., and Kelly, J. W. (2002) *Nat Rev Drug Discov.* (1), 267-275
10. Kaytor, M. D., and Warren, S. T. (1999) *J Biol Chem* 274(53), 37507-37510
11. Ferrone, F. (1999) *Methods Enzymol* 309, 256-274
12. Bertoncini, C. W., Rasia, R. M., Lamberto, G. R., Binolfi, A., Zweckstetter, M., Griesinger, C., and Fernandez, C. O. (2007) *J Mol Biol* 372(3), 708-722
13. Hsia, A. Y., Masliah, E., McConlogue, L., Yu, G. Q., Tatsuno, G., Hu, K., Kholodenko, D., Malenka, R. C., Nicoll, R. A., and Mucke, L. (1999) *Proc. Natl. Acad. Sci. USA* (96), 3228-3233

14. Mucke, L., Masliah, E., Yu, G. Q., Mallory, M., Rockenstein, E. M., Tatsuno, G., Hu, K., Kholodenko, D., Johnson-Wood, K., and McConlogue, L. (2000) *J. Neurosci.* (20), 4050-4058
15. Ashe, K. H. (2001) *Learn. Mem.* (8), 301-308
16. Klein, W. L., Krafft, G. A., and Finch, C. E. (2001) *Trends Neurosci.* (24), 219-224
17. Westerman, M. A., Cooper-Blacketer, D., Mariash, A., Kotilinek, L., Kawarabayashi, T., Younkin, L. H., Carlson, G. A., Younkin, S. G., and Ashe, K. H. (2002) *J Neurosci* (22), 1858-1867
18. Lesne, S., Koh, M., T., Kotilinek, L., Kayed, R., Glabe, C., G., Yang, A., Gallagher, M., and Ashe, K. H. (2006) *Nature* (440), 352-357
19. Form, L. S. (1996) *J Neuropathol Exp Neurol* 55(3), 259-272
20. Thomas, B., and Beal, M. F. (2007) *Hum Mol Genet.* 16 Spec No. 2, R183-194
21. Lotharius, J., and Brundin, P. (2002) *Nat Rev Neurosci* 3(12), 932-942
22. Spillantini, M. G., Schmidt, M. L., Lee, V. M., Trojanowski, J. Q., Jakes, R., and Goedert, M. (1997) *Nature* 388(6645), 839-840
23. Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papapetropoulos, T., Johnson, W. G., Lazzarini, A. M., Duvoisin, R. C., Di Iorio, G., Golbe, L. I., and Nussbaum, R. L. (1997) *Science* 276(5321), 2045-2047
24. Waxman, E. A., and Giasson, B. I. (2008) *Biochim Biophys Acta*
25. Davidson, W. S., Jonas, A., Clayton, D. F., and George, J. M. (1998) *J Biol Chem* 273(16), 9443-9449
26. Weinreb, P. H., Zhen, W., Poon, A. W., Conway, K. A., and Lansbury, P. T., Jr. (1996) *Biochemistry* 35(43), 13709-13715
27. El-Agnaf, O. M., Paleologou, K. E., Greer, B., Abogrein, A. M., King, J. E., Salem, S. A., Fullwood, N. J., Benson, F. E., Hewitt, R., Ford, K. J., Martin, F. L., Harriott, P., Cookson, M. R., and Allsop, D. (2004) *Faseb J* 18(11), 1315-1317
28. Biere, A. L., Wood, S. J., Wypych, J., Steavenson, S., Jiang, Y., Anafi, D., Jacobsen, F. W., Jarosinski, M. A., Wu, G. M., Louis, J. C., Martin, F., Narhi, L. O., and Citron, M. (2000) *J Biol Chem* 275(44), 34574-34579
29. Hashimoto, M., Hsu, L. J., Xia, Y., Takeda, A., Sisk, A., Sundsmo, M., and Masliah, E. (1999) *Neuroreport* 10(4), 717-721
30. Jensen, P. H., Sorensen, E. S., Petersen, T. E., Gliemann, J., and Rasmussen, L. K. (1995) *Biochem J* 310 (Pt 1), 91-94
31. Uversky, V. N., Li, J., Souillac, P., Millett, I. S., Doniach, S., Jakes, R., Goedert, M., and Fink, A. L. (2002) *J Biol Chem* 277(14), 11970-11978
32. Windisch, M., Hutter-Paier, B., Schreiner, E., and Wronski, R. (2004) *J Mol Neurosci* 24(1), 155-165
33. Volles, M. J., and Lansbury, P. T., Jr. (2007) *J Mol Biol* 366(5), 1510-1522
34. Tsigelny, I. F., Bar-On, P., Sharikov, Y., Crews, L., Hashimoto, M., Miller, M. A., Keller, S. H., Platoshyn, 0., Yuan, J. X., and Masliah, E. (2007) *Febs J* 274(7), 1862-1877
35. Azriel, R., and Gazit, E. (2001) *J. Biol. Chem.* (276), 34156-34161
36. Gazit, E. (2002) *Bioinformatics* (18), 880-883
37. Porat, Y., Kolusheva, S., Jelinek, R., and Gazit, E. (2003) *Biochemistry* (42), 10971-10977
38. Mazor, Y., Gilead, S., Benhar, I., and Gazit, E. (2002) *J. Mol. Biol.* (322), 1013-1024
39. Reches, M., and Gazit, E. (2003) *Science* (300), 625-627
40. Reches, M., and Gazit, E. (2004) *Amyloid* (11), 81-89
41. Lev, N., Melamed, E., and Offen, D. (2006) *Neurosci Lett* 399(1-2), 27-32
42. Feany, M. B., and Bender, W. W. (2000) *Nature* 404 (6776), 394-398
43. Ueda, K., Fukushima, H., Masliah, E., Xia, Y., Iwai, A., Yoshimoto, M., Otero, D. A., Kondo, J., Ihara, Y., and Saitoh, T. (1993) *Proc Natl Acad Sci USA* 90(23), 11282-11286
44. Kessler, J. C., Rochet, J. C., and Lansbury, P. T., Jr. (2003) *Biochemistry* 42(3), 672-678
45. Lee, H. J., Patel, S., and Lee, S. J. (2005) *J Neurosci* 25(25), 6016-6024
46. Lee, H. J., Suk, J. E., Bae, E. J., Lee, J. H., Paik, S. R., and Lee, S. J. (2008) *Int J Biochem Cell Biol* 40(9), 1835-1849

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated peptide being less than 20 amino acids in length, the peptide comprising an amino acid sequence GVLYVGSKTREGV (SEQ ID NO: 12) AAATGLVKREE (SEQ ID NO: 13) or GVVAAAEKTKQG (SEQ ID NO: 14), the peptide being capable of inhibiting alpha synuclein aggregation.

2. The peptide of claim 1, comprising at least one aromatic amino acid.

3. The peptide of claim 1, comprising at least one basic amino acid.

4. The peptide of claim 1, comprising at least one beta-breaker amino acid.

5. The peptide of claim 4, wherein said beta-breaker amino acid is a synthetic amino acid.

6. The peptide of claim 4, wherein said beta-breaker amino acid is naturally occurring.

7. The peptide of claim 1, wherein said amino acid sequence comprises at least one D-amino acid residue.

8. The peptide of claim 1, having an end cap modification.

9. A pharmaceutical composition comprising as an active ingredient the peptide of claim 1 and a pharmaceutically acceptable carrier.

10. A method of inhibiting alpha-synuclein aggregation, the method comprising contacting alpha-synuclein with the peptide of claim 1, thereby inhibiting alpha-synuclein aggregation.

11. A method of treating a medical condition associated with alpha-synuclein aggregation, the method comprising administering to a subject in need thereof a therapeutically effective amount of the peptide of claim 1, thereby treating the medical condition associated with alpha-synuclein aggregation.

12. The method of claim 11, wherein said medical condition is selected from the group consisting of Parkinson's disease (PD), Alzheimer's disease (AD), diffuse Lewy body disease, mixed AD-PD, multiple system atrophy and Hallervorden-Spatz disease.

13. A method of detecting alpha-synuclein monomers, the method comprising:
(a) contacting a biological sample selected suspected of comprising said alpha-synuclein monomers with the peptide of claim 1 under conditions which allow complex formation between said monomers and said peptide; and
(b) detecting presence or level of said complex, thereby detecting alpha-synuclein monomers.

* * * * *